(12) United States Patent
Anderson et al.

(10) Patent No.: US 7,732,206 B2
(45) Date of Patent: Jun. 8, 2010

(54) OLIGODENDROCYTE DETERMINATION GENES AND USES THEREOF

(75) Inventors: David J. Anderson, Altadena, CA (US); Qiao Zhou, Somerville, MA (US)

(73) Assignee: California Institute of Technology, Pasadena, CA (US)

( * ) Notice: Subject to any disclaimer, the term of this patent is extended or adjusted under 35 U.S.C. 154(b) by 608 days.

(21) Appl. No.: 11/397,200

(22) Filed: Apr. 4, 2006

(65) Prior Publication Data

US 2007/0025975 A1 Feb. 1, 2007

Related U.S. Application Data

(60) Provisional application No. 60/668,032, filed on Apr. 4, 2005.

(51) Int. Cl.
*C12N 15/00* (2006.01)
*C12N 5/071* (2010.01)
*C12N 5/00* (2006.01)

(52) U.S. Cl. ............... 435/455; 435/368; 435/375; 435/377

(58) Field of Classification Search ............. None
See application file for complete search history.

(56) References Cited

U.S. PATENT DOCUMENTS

2004/0014210 A1* 1/2004 Jessell et al. ............ 435/368

OTHER PUBLICATIONS

Sun et al., Current Biology, 11(18): 1413-1420, Sep. 18, 2001.*
Ryan and Federoff, Expert Opinion in Biological Therapy, 7(3): 305-318, Mar. 2007.*
Gabay et al., "Deregulation of Dorsoventral Patterning by FGF Confers Trilineage Differentiation Capacity on CNS Stem Cells in Vitro", Neuron 40: 485-499 (2003).
Fu et al, "Dual origin of spinal oligodendrocyte progenitors and evidence for the cooperative role of Olig2 and Nkx2.2 in the control of oligodendrocyte differentiation", Development 129: 681-693 (2002).
Arnett et al, "bHLH Transcription Factor Olig1 is Required to Repair Demyelinated Lesions in the CNS", Science 306: 2111-2115 (2004).
Gokhan et al, "Combinatorial Profiles of Oligodendrocyte-Selective Classes of Transcriptional Regulators Differentially Modulate Myelin Basic Protein Gene Expression", Journal of Neuroscience 25(36): 8311-8321 (2005).
Qi et al, "Control of oligodendrocyte differentiation by the Nkx2.2 homeodomain transciption factor", Development 126: 2723-2733 (2001).
Zhou et al, "Identification of a Novel Family of Oligodendrocyte Lineage-Specific Basic Helix-Loop-Helix Transcription Factors", Neuron 25: 331-343 (2000).
Zhang et al, "Induction of Oligodendrocytes from Adult Human Olfactory Epithelial-Derived Progenitors by Transcription Factors", Stem Cells 23: 442-453 (2005).
Zhou et al, "The bHLH Transcription Factors OLIG2 and OLIG1 Couple Neuronal and Glial Subtype Specification", Cell 109: 61-73 (2002).
Zhou et al, "The bHLH Trancirpiton Factor Olig2 Promotes Oligodendrocyte Differentiation in collaboration with Nkx2.2", Neuron 31: 791-807 (2001).

* cited by examiner

*Primary Examiner*—John D. Ulm
*Assistant Examiner*—Stacey MacFarlane
(74) *Attorney, Agent, or Firm*—McCarter & English, LLP

(57) ABSTRACT

The invention relates to methods and reagents for promoting the differentiation of oligodendrocytes from stem cells, by co-activating the Olig genes and the Nkx2.2 genes, and the use of the differentiated oligodendrocytes thus obtained in treating diseases, such as Multiple Sclerosis (MS). The invention also relates to the use of OLPs and oligodendrocytes thus obtained for drug screening.

9 Claims, 1 Drawing Sheet

OLIGODENDROCYTE DETERMINATION GENES AND USES THEREOF

REFERENCE TO RELATED APPLICATION

This application claims the benefit of the filing date of U.S. Provisional Applications U.S. Ser. No. 60/668,032, filed on Apr. 4, 2005. The teachings of the referenced application are incorporated herein by reference.

GOVERNMENT SUPPORT

Work described herein was funded, in whole or in part, by Grant No. RO1 NS23476 from the National Institute of Health (NIH). The United States government has certain rights in the invention.

BACKGROUND OF THE INVENTION

Oligodendrocytes are the myelinating glial cells of the central nervous system (CNS). The appearance of these myelinating cells during evolution is thought to have enabled the vertebrate nervous system to grow large and complex by allowing saltatory conduction of nervous impulses. These cells arise at discrete places and at discrete times from the ventricular zone of the developing neural tube. The molecular mechanisms that control the initial decision of multipotent CNS neural stem cells to become oligodendrocytes are not fully understood. Some growth factors have been identified that seem to bias stem cells towards an oligodendrocyte (ODC) fate.

Oligodendrocytes and their precursors (oligodendrocyte precursors or OLPs) are highly relevant to human disease. Deficiencies in the number, function or survival of these cells can cause devastating demyelinating diseases. A variety of demyelinating diseases exist in humans, wherein the myelin sheaths are lost, usually through the death of mature oligodendrocytes. One principal example, multiple sclerosis (MS). On the other hand, oncogenic transformation and overproduction of cells in this lineage, conversely, leads to brain tumors such as oligodendrogliomas and glioblastoma multiforme.

Multiple Sclerosis (MS) is an inflammatory disease of the Central Nervous System (CNS). Multiple Sclerosis affects roughly two and a half million people worldwide and is one of the most common causes of neurological disability in young adults. Typically, patients with MS present with a relapsing/remitting form of the disease, characterized by acute demyelinating episodes followed by the generation of new oligodendrocytes, remyelination, and functional recovery. However, remyelination is an inconsistent event in this disease, and the accumulated load of lesions that fail to remyelinate results in progressive neurological deterioration, in part because the capacity to generate new oligodendrocytes becomes limited.

Predominantly, it is a disease of the "white matter" tissue, which comprises nerve fibres responsible for transmitting communication signals both internally within the CNS and between the CNS and the nerves supplying rest of the body. In MS patients, patches of damage or "plaques or lesions" appear in seemingly random areas of the CNS white matter. At the site of a lesion, a nerve insulating material—myelin— is lost. Clinically, MS is a hard condition to characterize because it is very unpredictable and variable. Depending on which areas of the CNS are affected and how badly they are damaged, the type and severity of symptoms can vary greatly. No two people get MS in exactly the same way, and the expression of each individual's disease is as unique as their fingerprints. However, the different courses of the disease, both within an individual and within the whole population, principally differ in their timing, location and severity. Underneath similar processes (including demyelination and sometimes other forms of nerve degeneration) are going on.

Although recent research indicates that the biochemical make-up of lesions may vary between different forms of the disease, this is not the reason why people with MS (PwMS) have such widely differing symptoms—it's because nerve damage to one site usually causes completely different symptoms than damage to another. In general, MS patients can experience partial or complete loss of any function that is controlled by, or passes through, the brain or spinal cord.

There is still no cure for MS, although there are various strategies available to modify the disease course, treat exacerbations, manage symptoms, and improve function and safety. In combination, these treatments enhance the quality of life for people living with MS.

Oligodendrogliomas comprise a class of glial tumors in which the oligodendroglial cell is the cell predominant cell type. Normally, oligodendroglial cells form myelin—the fatty substance which surrounds the axons of nerve cells and provides the insulation which makes nerve cell electrical transmission faster and more efficient. Oligodendrogliomas probably evolve from a mixed glioma which has in turn evolved from primitive precursor or stem cells. The mixed glioma which contains astrocytic and neuronal elements as wells as oligodendroglial cells and is a slow growing tumor. But each of the cell types has a certain percentage of cells capable of mitosis. In the oligodendroglioma the mitotic rate of the oligodendroglial cells has exceeded the mitotic rate of the other cells and eventually the oligodendroglial cells become the most numerous—the predominant cell type and, therefore, an oligodendroglioma.

The speed of this transformation varies widely from patient to patient and there is no consistent way of predicting the behavior of any oligodendroglioma—especially in adult patients. In general, all glial tumors, including oligodendrogliomas, will become malignant, as a matter of time and random evolution in the ability of cells within that tumor to increase their rate of mitosis. The length of time could be 30 years, or it could be 6 months.

Glioblastoma multiforme refers to a malignant neoplasm with abundant glial pleomorphism, numerous mitotic figures and giant cells, vascular hyperplasia, and focal areas of necrosis. Occurring most commonly in the fifth through seventh decades, glioblastoma multiforme usually develops in the cerebral hemispheres (more often in the frontal lobes than the temporal lobes or basal ganglia) but almost never in the cerebellum. It grows as an irregular mass in the white matter and infiltrates the surrounding parenchyma by coursing along white matter tracts, frequently involving the corpus callosum and crossing the midline to produce the characteristic "butterfly" appearance.

Forty to fifty percent of primary central nervous system tumors are gliomas. Approximately 50% of these are glioblastoma multiforme, and 7% are astrocytomas. Oligodendrogliomas and glioblastoma multiforme are some of the most aggressive and intractable forms of cancer known. The prognosis is very poor. Mean survival length after diagnosis is eight to ten months, with less than 10% survival after two years. Unfortunately, the treatments for either of these classes of diseases, at present, are inadequate and unsatisfactory.

Therefore, there is a need to provide additional treatment methods and reagents for diseases related to oligodendrocytes, including demyelination diseases such as MS, and hyperproliferation diseases such as oligodendrogliomas and glioblastoma multiforme.

SUMMARY OF THE INVENTION

One aspect of the invention provides a method to enhance the differentiation of a cell from a mammal to an oligodendrocyte precursor (OLP) or an oligodendrocyte (ODC), comprising co-expressing in the cell an Olig gene and an Nkx2.2 gene.

In one embodiment, the mammal is a human. In other embodiment, the mammal is a non-human animal (such as non-human primates; farm animals, pet animals, lab animals, etc.).

In one embodiment, the cell is a neural stem cell, a neural progenitor cell, or an embryonic stem cell. The neural stem cell may grow in a monolayer culture, or grow as a proliferating cell in a neurosphere.

In one embodiment, the cell is a(an): embryonic progenitor cell, peripheral stem/progenitor cell, adult stem/progenitor cell, hematopoietic stem/progenitor cell, bone marrow stromal cell or mesenchymal stem cell, epithelium cell (such as olfactory epithelial cell), ectodermal-lineage cell (e.g., ectoderm-derived cell), especially neural ectodermal cell, CNS-derived cell or PNS-derived cell (such as schwann cell), de-differentiated adult cell, or anucleated oocyte transplanted with a nucleus. Certain of these cells may also be obtained from transgenic animals, which express certain transgenes (e.g., the subject Olig gene and/or Nkx2.2 gene) constitutively or inducibly.

In one embodiment, the cells is capable of differentiating into an OLP or ODC. In certain embodiments, the cell is also capable of differentiating into a neuron and/or an astrocyte.

In one embodiment, the OLP or ODC expresses O4, galactocerebroside (GalC), PLP/DM20, PDGFRαa, Sox10, GST-π, CNP (2'3'-cyclic nucleotide-3'-phospho-hydrolase), RIP (oligodendrocyte specific molecule), and/or myelin basic protein (MBP).

In one embodiment, the Olig gene is a polynucleotide encoding an Olig polypeptide at least about 90%, 91%, 92%, 93%, 94%, 95%, 96%, 97%, 98%, 99%, or about 100% identical to the Olig1, Olig2, and/or Olig3 proteins of the mammal or a different mammal, and the Olig polypeptide enhances cell differentiation to OLP or ODC when co-expressed with the Nkx2.2 gene. In one embodiment, the Olig gene is the Olig1, Olig2, or Olig3 protein of the mammal, or the Olig1, Olig2, or Olig3 protein of a different mammal.

In one embodiment, the Nkx2.2 gene is a polynucleotide encoding a polypeptide at least about 90%, 91%, 92%, 93%, 94%, 95%, 96%, 97%, 98%, 99%, or about 100% identical to the Nkx2.2 or Nkx2.5 protein of the mammal, and the polypeptide enhances cell differentiation to OLP or ODC when co-expressed with the Olig gene.

In one embodiment, the Olig gene and/or the Nkx2.2 gene are endogenous genes of the cell. In one embodiment, the Olig gene and/or the Nkx2.2 gene are exogenous genes of the cell.

In one embodiment, the exogenous Olig gene and/or the exogenous Nkx2.2 gene are under the control of a constitutive promoter or an inducible promoter.

In one embodiment, the Olig gene and/or the Nkx2.2 gene are transgenes. The Olig gene and/or the Nkx2.2 gene may be tagged (for example, by GFP or other fluorescent moieties) for monitoring treatment results.

In a related aspect, the invention provides a method to enhance the differentiation of a cell from a mammal to an oligodendrocyte precursor (OLP) or an oligodendrocyte (ODC), comprising co-expressing in the cell an Olig gene and an Nkx2.2 substitute gene, such as a Notch/Delta pathway gene, an upstream gene that activates Nkx2.2 or Nkx2.5, a downstream gene activated by Nkx2.2 or Nkx2.5, an antagonist of an inhibitor of Nkx2.2 or Nkx2.5. Preferably, the substitute gene functionally replaces the Nkx2.2 gene in co-operating with the Olig gene to enhance OLP/ODC differentiation.

In a related aspect, the invention provides a method to enhance the differentiation of a cell from a mammal to an oligodendrocyte precursor (OLP) or an oligodendrocyte (ODC), comprising co-expressing in the cell an Nkx2.2 gene and an Olig substitute gene, such as an upstream gene that activates Olig1, Olig2, or Olig3 (e.g., a FGF gene such as FGF-2, or a hedgehog gene such as Shh), a downstream gene activated by Olig1, Olig2, or Olig3 (such as Sox9 or Sox10), an antagonist of an inhibitor of Olig1, Olig2, or Olig3 (such as BMP4 and other BMPs, Id2 or Id4), etc. Preferably, the substitute Olig gene functionally replaces the Olig gene in co-operating with the Nkx2.2 gene to enhance OLP/ODC differentiation.

Another aspect of the invention provides a method of treating a mammalian individual suffering from a disease associated with demyelination of central nervous system axons, comprising administering to the individual OLPs or ODCs differentiated therefrom using the subject methods, in an amount effective to treat the disease.

In a related aspect, the invention provides a method of treating a mammalian individual suffering from a disease associated with demyelination of central nervous system axons, comprising: (1) using the method of claim 1, differentiating mammalian cells to OLPs or ODCs; (2) introducing the OLPs or ODCs to the mammalian individual, in an amount effective to treat the disease.

In one embodiment, the mammalian individual is a human.

In one embodiment, the OLPs or ODCs are administered to the mammalian individual by cell transplantation. In one embodiment, the differentiated OLPs or ODCs are proliferated in vitro prior to cell transplantation.

In one embodiment, the method further comprising co-administering to the mammalian individual a second pharmaceutical composition effective for treating the disease.

In one embodiment, the second pharmaceutical composition, which may be those as described in U.S. Pat. Nos. 6,613,756; 6,569,431; 6,548,061; 6,492,427; 6,150,345; 6,333,033; 6,274,136; 6,268,340; 6,203,788; 5,885,584; 5,219,837 & 5,574,009.

In one embodiment, the disease is multiple sclerosis, acute disseminated encephalomyelitis, transverse myelitis, demyelinating genetic disease, spinal cord injury, virus-induced demyelination, Progressive Multifocal Leucoencephalopathy, Human Lymphotrophic T-cell Virus I (HTLVI)-associated myelopathy, or nutritional metabolic disorder.

In one embodiment, the mammalian cells are obtained from a mammalian species different from that of the mammalian individual. In other embodiment, the mammalian cells are obtained from the same mammalian species of the mammalian individual, preferably, the mammalian cells are obtained from another individual with a matching allotype, or from the same mammalian individual to minimize the risk of allograft rejection.

In a related aspect, the invention provides a method of treating a mammalian individual suffering from a disease associated with demyelination of central nervous system axons, comprising: inducing in vivo co-expression of an Olig protein and an Nkx2.2 or Nkx2.5 protein in neural stem cells or neural progenitor cells of the mammalian individual to direct the differentiation of the neural stem/progenitor cells to OLPs or ODCs.

In one embodiment, the co-expression is effectuated by introducing Olig and/or Nkx2.2 or Nkx2.5 proteins into neural stem/progenitor cells in the ventricular zone via transcytosis.

In one embodiment, the co-expression is effectuated by introducing vectors (such as retroviral vectors or adenovirus based vectors) encoding Olig and/or Nkx2.2 or Nkx2.5 proteins into neural stem/progenitor cells in the ventricular zone.

Another aspect of the invention provides a method of screening for an antagonist for OLP or ODC differentiation, comprising: (1) providing a cell from a mammal, said cell capable of differentiating into OLP or ODC according to the subject method, (2) contacting the cell with a candidate compound, (3) assessing the ability and/or degree of the candidate compound to antagonize the differentiation of the cell to OLP or ODC according to the subject method, wherein the candidate compound is an antagonist for OLP or ODC differentiation if the candidate compound delays or inhibits OLP or ODC differentiation.

In one embodiment, step (3) is effectuated by the presence and/or extent of OLP/ODC marker expression.

Another aspect of the invention provides a screening method for identifying an antagonist for oligodendrocyte (ODC) proliferation, comprising: (1) contacting a candidate compound with an OLP or ODC differentiated according to the subject method, and, (2) comparing the proliferation of the OLP or ODC before and after contacting the candidate compound, wherein a reduced proliferation rate indicates that the candidate compound is a potential growth inhibitor of the OLP or ODC.

In one embodiment, the method further comprises assessing the general toxicity of the antagonist thus identified on one or more of other cell types selected from: neuron, astrocyte, epithelial cell, endothelial cell, and fibroblast, wherein the antagonist is a selective antagonist of OLP or ODC proliferation if the antagonist is substantially more effective in inhibiting the proliferation of OLP or ODC than the other cell types.

In one embodiment, the antagonist is at least 50% more effective in inhibiting OLP or ODC proliferation than inhibiting the proliferation of one of said other cell types.

In one embodiment, the method further comprises assessing the in vitro and/or in vivo killing effect of the antagonist thus identified on established cancers or cancer cell lines.

In one embodiment, the cancers are oligodendrogliomas or glioblastoma multiforme.

Yet another embodiment of the invention provides a method to treat a hyperproliferative disease characterized by overexpression of an Olig gene, the method comprising inducing co-expression of an Nkx2.2 gene in the disease cell or tissue to promote the differentiation of the disease cell or tissue.

This aspect of the invention is partly based on the discovery that co-expression of a subject Olig gene and a subject Nkx2.2 gene promotes cell differentiation to OLP or ODC, which may exit mitotic cycle by virtue of the initiation of the differentiation program.

In one embodiment, the hyperproliferative disease is cancer, such as oligodendrogliomas or glioblastoma multiforme.

The different embodiments of the invention, including those described under different aspects of the invention, are contemplated to be applicable to all aspects of the invention when appropriate. Any embodiment of the invention is also contemplated to be able to combine with other embodiments of the invention whenever non-prohibited.

DETAILED DESCRIPTION OF THE INVENTION

1. Overview

Figure 1:
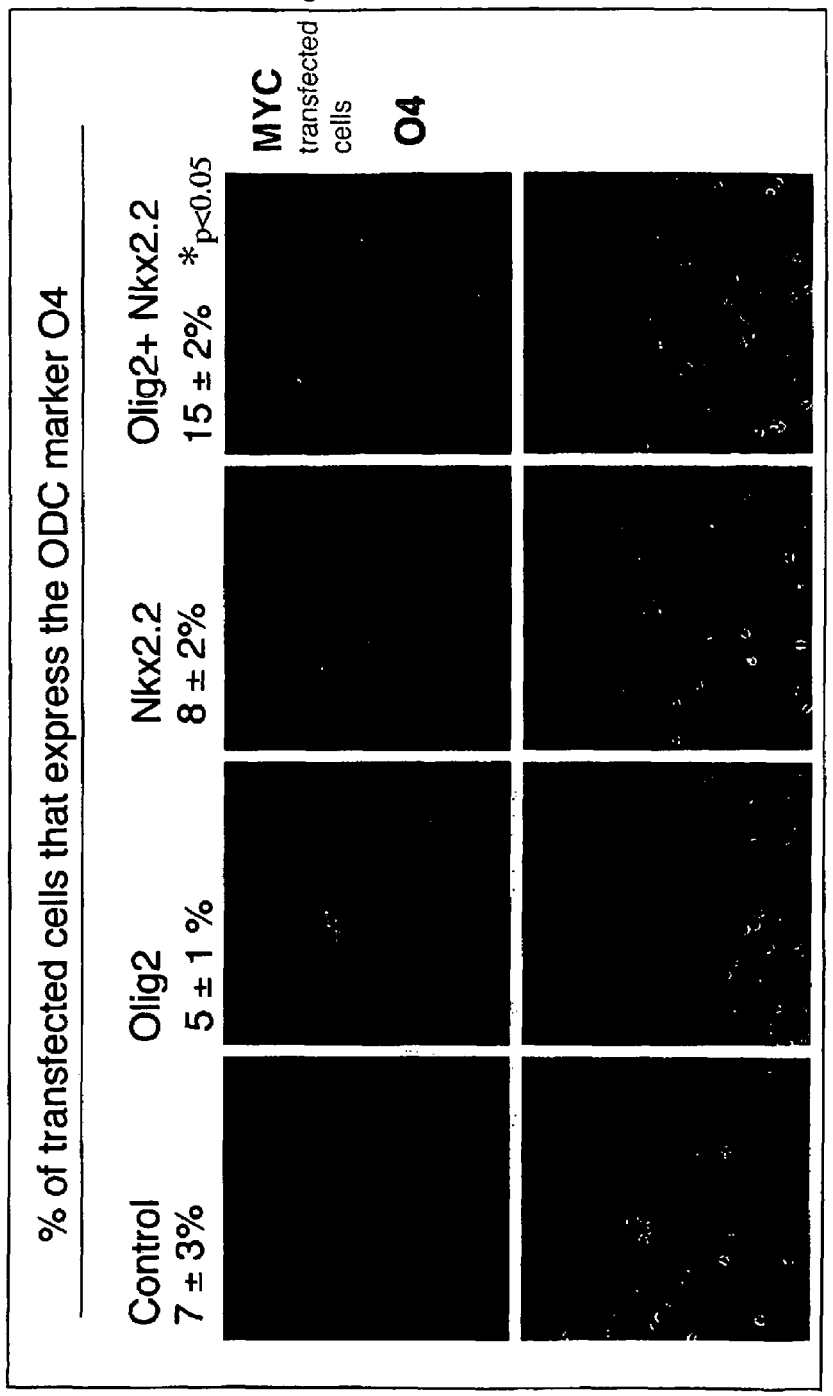
FIG. 1 shows that co-expression of Olig2 and Nkx2.2 in cultured spinal cord neural stem cells promotes oligodendrocyte (ODC) differentiation. The percentage of cells that were co-transfected with the two genes and expressed the ODC marker O4 was indicated above each columns of panels. The control cells, cells only transfected by Olig2, and cells only transfected by Nkx2.2 contain only 7%, 5%, and 8%, respectively, of O4-expressing cells. However, in cells co-transfected by both genes, the % of O4-expressing cells is 2-3 times higher (at 15%), which is significantly higher ($P<0.05$).

In the spinal cord, neurons, astrocytes, and oligodendrocytes constitute the three fundamental cell types of the central nervous system. This basic triad comprises many hundreds or even thousands of distinct neuronal subtypes, in addition to subtypes of astroglia and perhaps of oligodendroglia as well.

Two major classes of transcription factors have emerged as determinants of neuron versus glial fate determination and of neuron subtype specification: the basic-helix-loop-helix (bHLH) factors and homeodomain (HD) factors, respectively. In vertebrates, bHLH factors homologous to the *Drosophila* proneural genes, such as the Neurogenins (Ngns) and Mash1, promote neuronal differentiation at the expense of the glial fate. In the spinal cord, a combinatorial code of HD transcription factors specifies the regional identity of progenitor domains along the dorso-ventral axis. Motoneurons are generated from the pMN domain, while V0, V1, V2, and V3 interneurons are generated from the p0, p1, p2, and p3 domains, respectively. This discontinuous patterning arises from mutually repressive interactions between the HD factors that specify adjacent progenitor domains.

Applicants have identified a subclass of neural bHLH factors, the Olig genes. In the mouse, there are two Olig genes that are specifically expressed in oligodendrocyte precursors (OLPs), called Olig1 and Olig2, while in the chick, a single gene orthologous to Olig2 has been identified. In the spinal cord, OLPs emerge from a highly restricted domain of the ventral ventricular zone, which is precisely demarcated by expression of Olig1 and Olig2.

Prior to oligodendrogliogenesis, the domain of Olig2 expression corresponds to the pMN domain, from which motoneurons are generated. Gain-of-function experiments suggest that Olig2 plays a determinative role in patterning the pMN domain and also initiates motoneuron differentiation and cell cycle arrest, in part by promoting expression of Ngn2. These data suggest that Olig2 sequentially controls both motoneuron and oligodendrocyte fate determination. Indeed, Applicants found that in the absence of Olig1/2 function in double-homozygous mice, presumptive motoneuron precursors are transformed into V2 interneuron precursors, and oligodendrocytes are lost throughout the brain and spinal cord. In other words, the sequential production of motoneurons and oligodendrocytes is converted into the sequential production of interneurons and astrocytes, suggesting that Olig genes couple neuronal and glial subtype specification. Thus the Olig1 and Olig2 genes, together with other proneural genes, comprise a combinatorial code for the specification of neurons, astrocytes, and oligodendrocytes.

In developing chicken embryo, Olig2 is sufficient to cause ectopic differentiation of oligodendrocytes in the spinal cord when misexpressed together with the HD factor Nkx2.2. However, prior to the instant invention, it was unclear whether Nkx2.2 and Olig2 might also collaborate to promote oligodendrocyte differentiation from various types of mammalian cells (such as mammalian embryonic stem cells or ES cells, neural stem cells or neural progenitor cells, epithelial cells, etc.), originating either from embryos, post-natal or adult tissues.

Part of the reasons for this uncertainty is that there are major differences in the way that the Olig genes and Nkx2.2 are regulated during oligodendrocyte fate specification in birds (e.g., chick) and in mammals (e.g., mouse and human). Another major reason is that many developmental events are not repeated in post-natal or adult tissues. Specifically, during chicken development, Olig2 and Nkx2.2 are coexpressed in the ventricular zone (stem cell-containing region) of the spinal cord, before oligodendrocyte progenitors migrate out of this region, whereas in mammalian development, such as in rat and mouse embryos, there is no Olig2 and Nkx2.2 co-expression in the ventricular zone prior to the emergence of OLPs from this region. Specifically, mammalian embryonic Olig2⁺ OLPs or ODCs do not detectably co-express Nkx2.2 when they first migrate out of the ventricular zone, when they have already become OLPs or ODCs, as evidenced by their expression of OLP markers such as PDGFRα (PDGF Receptor-α).

Thus, prior to the instant invention, it was unclear whether the Olig genes and the Nkx2.2 genes would collaborate in mammalian cells to promote oligodendrocyte fate specification, in the same way that they do in avian species.

To the best knowledge of the Applicants, the instant invention provides the first evidence that Olig genes and Nkx2.2 genes, when co-expressed in mammalian cells (such as ES cells, neural stem cells or progenitor cells), stimulates and enhances the differentiation of these stem cells into oligodendrocyte precursor (OLP) and oligodendrocytes (ODC).

Thus one aspect of the invention provides a method to differentiate a mammalian cell to an OLP or oligodendrocyte (ODC), comprising inducing the co-expression of an Olig gene and an Nkx2.2 gene. The induced co-expression may be achieved through various means, including co-expression of exogenous genes in a target mammalian cell, or release the inhibition of the endogenous Olig gene and the Nkx2.2 gene to allow their co-expression in the target cell.

The method of the invention is applicable for cells of mammalian origin. Target cells include (but are not limited to): neural stem cells, neural progenitor cells, embryonic stem cells, embryonic progenitor cells, peripheral stem/progenitor cells, adult stem/progenitor cells, hematopoietic stem/progenitor cells, bone marrow stromal cells or mesenchymal stem cells, epithelium cells (such as olfactory epithelial cells), ectodermal-lineage cells (e.g., ectoderm-derived cells), especially neural ectodermal cells, CNS-derived cells or PNS-derived cells (such as schwann cells), de-differentiated adult cells, or anucleated oocyte transplanted with a nucleus. Certain of these cells may also be obtained from transgenic animals, which express certain transgenes (e.g., the subject Olig gene and/or Nkx2.2 gene) constitutively or inducibly.

In certain embodiments, the target cell are totipotent stem cells. In other embodiments, the target cells are pluripotent progenitor cells. In certain embodiments, the target cell has preserved the potential to differentiate into ODCs or OLPs.

These mammalian cells may be obtained from embryonic, post-natal or adult tissues, such as those obtained from biopsy, surgery, or cadaver, discarded embryonic tissues from infertility treatment center or discarded IVF embryos, etc.

The target cells may be primary cells freshly isolated from tissues, or those having only gone through a limited number of in vitro division. Alternatively, the target cells may be established cell lines.

For CNS-derived neural stem cells, the cells may grow in culture as a monolayer, or grow as small floating aggregates of proliferating cells known as neurospheres.

Isolation and maintenance of these mammalian cells are generally known in the art, or can be readily adapted from these known methods. For example, the neural stem/progenitor cells may be obtained from any suitable source, so long as the stem cell retains the potential to differentiate into OLP or oligodendrocyte. Numerous tissue or cell sources have been described to contain such stem cells, which are either totipotent or multi-potent. Exemplary sources/tissues, the isolation of neural stem cells from such sources/tissues, and the culturing and manipulation of the isolated stem cells are described below in detail.

Once obtained, the mammalian target cells (e.g., neural stem/progenitor cells or ES cells) may be induced to co-express an Olig gene and an Nkx2.2 gene, so that the cells differentiate into OLPs and oligodendrocytes. The Olig gene and/or the Nkx2.2 gene may be endogenous (e.g., when the cells are isolated from transgenic animals having Olig gene and/or the Nkx2.2 gene under the control of inducible promoters), or exogenously introduced into the cells (e.g., by tranfection or infection, etc.).

The cells can be primary or from cultures, adult or fetal origin. Moreover, while human cells are preferred, any mammalian cell can be used in this invention, including cells from mice, cattle, sheep, goat, pigs, dogs, rats, rabbits, and primates, etc.

According to the method of the invention, at least one Olig gene(s) and at least one Nkx2.2 gene(s) are co-expressed in the target cell. The subject Olig genes include Olig1, Olig2, Olig3. The subject Nkx2.2 gene includes Nkx2.2 and Nkx2.5. In certain embodiments, the subject Olig genes may be substituted by certain upstream genes that activates Olig1, Olig2, or Olig3 (e.g., FGF genes such as FGF-2, and hedgehog genes such as Shh, see Gabay et al., *Neuron* 40(3): 485-99, 2003), certain downstream genes that are activated by Olig1, Olig2, or Olig3 (such as Sox9 or Sox10), certain antagonists of the inhibitors of Olig1, Olig2, or Olig3 (such as BMP4 and other BMPs, Id2 or Id4). In certain embodiments, the subject Nkx2.2 genes may be substituted by certain upstream genes that activates Nkx2.2, or Nkx2.5, certain downstream genes that are activated by Nkx2.2, or Nkx2.5, certain antagonists of the inhibitors of Nkx2.2, or Nkx2.5. An exemplary Nkx2.2 substitute gene is a Notch/Delta pathway gene. Preferably, the substitute genes, upstream or downstream genes described herein can functionally replace the Olig genes or the Nkx2.2 genes they substitute.

The Olig and Nkx2.2 genes/proteins or their substitutes may be from human, other mammalian sequences, or their derivative sequences, which can be readily obtained by database sequence search using programs such as BLAST, or any modified/artificial sequences sharing at least about 80%, 85%, 90%, 91%, 92%, 93%, 94%, 95%, 96%, 97%, 98%, 99%, or nearing 100% identity to the subject genes, such as the human Olig1, Olig2, Olig3, Sox9, or Sox10; OR Nkx2.2, or Nkx2.5 genes/proteins, respectively (see below).

Certain marker genes may be used to assess the presence of OLP or ODC cells. An exemplary but non-limiting list of such OLP or ODC markers include: O4, galactocerebroside (GalC), PLP/DM20, PDGFRα, Sox10, GST-π, CNP (2'3'- cyclic nucleotide-3'-phospho-hydrolase), RIP (oligodendrocyte specific molecule), or myelin basic protein (MBP), etc.

In certain embodiments, the OLPs or ODCs are further assessed by verifying the absence or substantial absence of expression of markers for neurons (such as neuron-specific βIII tubulin or TuJ 1) and astrocytes (such as Glial Fibrillary Acidic protein or GFAP).

Another aspect of the invention provides a method of treating a mammalian individual suffering from a disease associated with demyelination of central nervous system axons, comprising administering to the individual OLPs or oligodendrocytes differentiated therefrom using the methods of the invention, in an amount effective to treat the disease associated with demyelination of central nervous system axons.

In one embodiment, the disease associated with demyelination of central nervous system axons may be selected from the group consisting of: multiple sclerosis, acute disseminated encephalomyelitis, transverse myelitis, demyelinating genetic diseases, spinal cord injury, virus-induced demyelination, Progressive Multifocal Leucoencephalopathy, Human Lymphotrophic T-cell Virus I (HTLVI)-associated myelopathy, and nutritional metabolic disorders.

Yet another aspect of the invention provides a screening method for identifying antagonists for oligodendrocyte proliferation, comprising contacting a candidate compound with a subject oligodendrocyte or OLP, and comparing the proliferation of the oligodendrocyte or OLP before vs. after contacting the candidate compound, wherein a reduced proliferation rate indicates that the candidate compound is a potential growth inhibitor of the subject oligodendrocyte or OLP.

In one embodiment, the method further comprising assessing the general toxicity of the antagonist thus identified on other cell types, such as neurons, astrocytes, epithelial cells, endothelial cells, and/or fibroblasts. The general toxicity may also be assessed using the original mammalian cell from which the OLPs or ODCs derive.

In one embodiment, the method further comprises assessing the in vitro and/or in vivo killing effect of the antagonist thus identified on established cancer or cancer cell lines, such as those from oligodendroglioma, or glioblastoma multiforme. The antagonist is a selective antagonist of OLP or ODC proliferation if the antagonist is substantially more effective in inhibiting the proliferation of OLP or ODC than the other cell types.

In one embodiment, the antagonist is at least 50%, 75%, 1-fold, 2-fold, 5-fold, 10-fold or more effective in inhibiting OLP or ODC proliferation than inhibiting the proliferation of one of said other cell types.

The effectiveness may be measured, for example, by $EC_{50}$, which represents the concentration of the candidate compound that gives rise to 50% of the maximum inhibition.

Another aspect of the invention provides a method of screening for an antagonist for OLP or ODC differentiation, comprising: (1) providing a cell (such as a neural stem/progenitor cell or ES cell) from a mammal, the cell capable of differentiating into OLP or ODC according to the subject method, (2) contacting the cell with a candidate compound, (3) assessing the ability and/or degree of the candidate compound to antagonize the differentiation of the cell to OLP or ODC according to the subject method, wherein the candidate compound is an antagonist for OLP or ODC differentiation if the candidate compound delays or inhibits OLP or ODC differentiation.

In one embodiment, step (3) is effectuated by the presence and/or extent of OLP/ODC marker expression (e.g., expression of O4, galactocerebroside (GalC), MBP, and/or any other OLP/ODC marker).

In one embodiment, step (3) is effectuated by the presence and/or extent of the cells exhibiting a characteristic oligodendrocyte morphology.

Yet another embodiment of the invention provides a method to treat a hyperproliferative disease characterized by overexpression of an Olig gene, the method comprising inducing expression of an Nkx2.2 gene in the disease cell or tissue to promote the differentiation of the disease cell or tissue. This aspect of the invention is partly based on the discovery that co-expression of a subject Olig gene and a subject Nkx2.2 gene promotes cell differentiation to OLP or ODC, which may exit mitotic cycle by virtue of the initiation of the differentiation program, and thus no longer proliferate uncontrollably.

In one embodiment, the hyperproliferative disease is cancer, such as oligodendrogliomas or glioblastoma multiforme.

Other features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

2. Culturing of Multipotent Neural Stem Cells and Their Progeny

It is well known in the art to culture multipotent neural stem cells, from which the subject oligodendrocyte precursors can be differentiated using the subject methods. Prior to the instant invention, neural stem cells have been isolated from fetal tissues, and subsequently differentiated into ODCs by, for example, growing in growth factors such as FGF-2 (Gabay et al., Neuron 40(3): 485-499, 2003). However, such process is extremely low in efficiency and expensive, thus making it impractical to generate large quantities of ODCs or OLPs for therapeutic and research uses. The methods of the invention overcome this problem, by providing a more efficient and cost-effective way of generating large quantities of ODCs or OLPs.

Although many cell types can be used as starting material for the subject methods, this section provides exemplary methods to obtain neural stem/progenitor cells for use in the instant invention. It should be understood, however, that the methods of the invention is not limited to neural stem/progenitor cells. In addition, it is well-known in the art that other cell types suitable for use in the instant invention can be readily obtained using established methods. See, for example, U.S. Pat. Nos. 5,843,780, 6,875,608, 6,887,706, 6,921,632, 7,005,252, 7,011,828, etc.

U.S. Pat. Nos. 5,750,376; 5,851,832; 5,980,885; 5,981,165; 6,071,889; 6,294,346; 6,399,369; and 6,497,872; and US 2003-0049837 A1, US 2003-0082515 A1; US 2003-0095956 A1; and US 2003-0109008 A1 (all incorporated herein by reference) describe methods for producing genetically modified neural cells, comprises culturing cells derived from embryonic, juvenile, or adult mammalian neural tissue with one or more growth factors that induce multipotent neural stem cells to proliferate and produce multipotent neural stem cell progeny, which include more daughter multipotent neural stem cells and undifferentiated progeny that are capable of differentiating into neurons, astrocytes, and oligodendrocytes. The proliferating neural cells can be transfected with exogenous DNA to produce genetically modified neural stem cell progeny. Using this method, these cultured multipotent neural stem cells and their undifferentiated progeny may be induced to co-express the Olig genes and Nkx2.2 to produce the subject OLPs and oligodendrocytes.

The multipotent neural stem cell progeny can be continuously passaged and proliferation reinitiated in the presence of growth factors to result in an unlimited supply of neural cells for transplantation and other purposes, such as drug screening. Culture conditions are provided that induce the genetically modified multipotent neural stem cell progeny to differentiate into neurons, astrocytes, and the subject OLPs and oligodendrocytes in vitro.

According to U.S. Pat. No. 5,750,376, methods for inducing multipotent neural stem cells from fetal, juvenile, or adult mammalian tissue to proliferate in vitro, in vivo, or in situ are provided, to generate large numbers of neural stem cell progeny capable of differentiating into neurons, astrocytes, and oligodendrocytes. The induction of proliferation (and differentiation) of neural stem cells can be done either by culturing the cells in suspension, or on a substrate onto which they can adhere. Alternatively, proliferation and differentiation of neural stem cells can be induced, under appropriate conditions, in the host in the following combinations: (1) proliferation and differentiation in vitro, then transplantation, (2) proliferation in vitro, transplantation, then further proliferation and differentiation in vivo, (3) proliferation in vitro, transplantation and differentiation in vivo, and (4) proliferation and differentiation in vivo. Proliferation and differentiation in vivo or in situ can involve a non-surgical approach that coaxes neural stem cells to proliferate in vivo with pharmaceutical manipulation.

These methods can be adapted for use in the instant invention, where neural stem cells may be isolated and cultured in vitro, to supply a large quantity of stem cells, which can be further induced/manipulated to differentiate into oligodendrocytes or OLPs for transplantation and other medical/research uses, such as large scale drug screening for compounds antagonizing the proliferation of oligodendrocytes. The following sub-section further describes different aspects of the methods.

A. Multipotent Neural Stem Cells

Neurobiologists have used various terms interchangeably to describe the undifferentiated cells of the CNS. Terms such as "stem cell," "precursor cell" and "progenitor cell" are commonly used in the scientific literature. However, there are different types of undifferentiated neural cells, with differing characteristics and fates. The terminology used for undifferentiated neural cells has evolved such that these cells are now termed "neural stem cells." Thus "progenitor" cell proliferated in vitro mean "an oligopotent or multipotent stem cell which is able to divide without limit and under specific conditions can produce daughter cells which terminally differentiate into neurons and glia." The capability of a cell to divide without limit and produce daughter cells which terminally differentiate into neurons and glia are stem cell characteristics. Accordingly, as used herein, the cells proliferated using the subject methods are termed "neural stem cells." A neural stem cell is an undifferentiated neural cell that can be induced to proliferate using the methods of the present invention. The neural stem cell is capable of self-maintenance, meaning that with each cell division, one daughter cell will also be a stem cell. The non-stem cell progeny of a neural stem cell are termed progenitor cells. The progenitor cells generated from a single multipotent neural stem cell are capable of differentiating into neurons, astrocytes (type I and type II) and oligodendrocytes. Hence, the neural stem cell is "multipotent" because its progeny have multiple differentiative pathways.

The term "neural progenitor cell," as used herein, refers to an undifferentiated cell derived from a neural stem cell, and is not itself a stem cell. Some progenitor cells can produce progeny that are capable of differentiating into more than one cell type. For example, an O-2A cell is a glial progenitor cell that gives rise to oligodendrocytes and type II astrocytes, and thus could be termed a "bipotential" progenitor cell. A distinguishing feature of a progenitor cell is that, unlike a stem cell, it has limited proliferative ability and thus does not exhibit self-maintenance. It is committed to a particular path of differentiation and will, under appropriate conditions, eventually differentiate into glia or neurons.

The term "precursor cells," as used herein, refers to the progeny of neural stem cells, and thus includes both progenitor cells and daughter neural stem cells.

Neural stem cell progeny can be used for transplantation into a heterologous, autologous, or xenogeneic host. Multipotent neural stem cells can be obtained from embryonic, post-natal, juvenile or adult neural tissue. The neural tissue can be obtained from any animal that has neural tissue such as insects, fish, reptiles, birds, amphibians, mammals and the like. The preferred source neural tissue is from mammals, preferably rodents and primates, and most preferably, mice and humans (preferably HLA-type matched human).

In the case of a heterologous donor animal, the animal may be euthanized, and the neural tissue and specific area of interest removed using a sterile procedure. Areas of particular interest include any area from which neural stem cells can be obtained that will serve to restore function to a degenerated area of the host's nervous system, particularly the host's CNS. Suitable areas include the cerebral cortex, cerebellum, midbrain, brainstem, spinal cord and ventricular tissue, and areas of the PNS including the carotid body and the adrenal medulla. Preferred areas include regions in the basal ganglia, preferably the striatum which consists of the caudate and putamen, or various cell groups such as the globus pallidus, the subthalamic nucleus, the nucleus basalis which is found to be degenerated in Alzheimer's Disease patients, or the substantia nigra pars compacta which is found to be degenerated in Parkinson's Disease patients. Particularly preferred neural tissue is obtained from ventricular tissue that is found lining CNS ventricles and includes the subependyma.

The term "ventricle" refers to any cavity or passageway within the CNS through which cerebral spinal fluid flows. Thus, the term not only encompasses the lateral, third, and fourth ventricles, but also encompasses the central canal, cerebral aqueduct, and other CNS cavities.

Human heterologous neural stem cells may be derived from fetal tissue following elective abortion, or from a post-natal, juvenile or adult organ donor. Autologous neural tissue can be obtained by biopsy, or from patients undergoing neurosurgery in which neural tissue is removed, for example, during epilepsy surgery, temporal lobectomies and hippocampalectomies. Neural stem cells have been isolated from a variety of adult CNS ventricular regions, including the frontal lobe, conus medullaris, thoracic spinal cord, brain stem, and hypothalamus, and proliferated in vitro using the methods detailed herein. In each of these cases, the neural stem cell exhibits self-maintenance and generates a large number of progeny which include neurons, astrocytes and oligodendrocytes.

Normally, the adult mammalian CNS is mitotically quiescent in vivo with the exception of the subependymal region lining the lateral ventricles in the forebrain. This region contains a subpopulation of constitutively proliferating cells with a cell cycle time of 12.7 hours. BrdU and retroviral labeling of the proliferating cells reveal that none of the newly generated cells differentiate into mature neurons or glia nor do they migrate into other CNS regions (Morshead and Van der Kooy, supra).

The continual proliferation and maintenance of a constant number of cells within the subependyma is explained by two mechanisms. The death of one of the daughter cells after each division maintains the proliferating population at a constant number. The constitutively dividing population eventually dies out (and hence is not a stem cell population) however, a subpopulation of relatively quiescent cells within the subependyma is able to repopulate the constitutively dividing population. This stem cell-like mode of maintaining the proliferative subependymal population is analogous to other tissues where cells have a short life span and are repopulated by a subpopulation of relatively quiescent cells referred to as stem cells.

Experiments utilizing retrovirus infection of constitutively proliferating cells in vivo and subsequent β-galactosidase (β-gal) reporter gene expression as a non-diluting marker show that with increasing adult mice survival times (of up to 28 days post retrovirus infection), there is a progressive loss of β-gal positive subependymal cells. Using nested PCR to identify single cells containing retroviral DNA, it was determined that the loss of β-gal expressing cells is due to the loss of the retrovirally infected cells through cell death, not due to the turn-off of β-gal expression.

Intraperitoneal injections of BrdU (a thymidine analog that is incorporated into the DNA of dividing cells) reveal that 33% of the cells within some regions of the subependyma make up the normally constitutively dividing population (see Morshead and van der Kooy, J. Neurosci. 12: 249, 1992). The number of BrdU labeled cells decreases over time. By 30 days after BrdU labeling, only 3% of the dividing cells are still labeled. The heavy labeling of only a small number of cells 30 days after BrdU injections demonstrates that although the labeled cells were dividing at the time of the injections they were relatively quiescent for the 30 day period. This suggests that these few labeled cells are stem cells rather than cells of the constitutively proliferating population.

The above two examples support the hypothesis that the maintenance of the constant number of proliferating subependymal cells seen throughout adult life requires the presence of a relatively quiescent stem cell that proliferates sporadically to replenish the constitutively proliferating population and to self-renew.

The constitutively dividing subependymal cells can be killed off by injecting high doses of radioactive thymidine for the duration of the cell cycle at intervals less than S-phase duration. At one day post-kill, the proliferating population is 10% of controls, and by 8 days, the proliferating population is back to control levels. If the replenished population is due to the recruitment of normally quiescent stem cells into the proliferative mode, then a second kill at the time that stem cells are generating progeny to repopulate the subependyma should alter the number of cells within the constitutively proliferating population. When a second kill is done 2 days after the initial kill, 8 days later the constitutively proliferating population is only 45% of the control values (animals receiving no thymidine kill treatment) or animals that received only one kill at day 0 (the time of the first kill). The reduction in the number of proliferative cells in the subependyma is maintained at 63% even at 31 days after the second kill. When a second kill is done on day 4, the proliferating population returns to 85% of control values 8 days later. These results suggest that the normally quiescent stem cell is recruited into the proliferative mode within the first two days after the initial kill and that by 4 days the stem cell no longer needs to be recruited to repopulate the subependyma.

An experiment was performed to determine whether the in vitro stem cell is derived from the constitutively proliferating population or from the quiescent population. The results demonstrate in adult, the stem cells which are proliferated in vitro are derived from the quiescent population of subependymal cells in vivo. This also explains why stem cells can be derived from CNS ventricular regions, other than the forebrain, which do not have a subpopulation of constitutively proliferating cells.

Numerous other patent literature also describe various totipotent, pluripotent/multipotent stem cells that have maintained their potential to develop or differentiate into OLPs or oligodendrocytes. All such cells/tissues may serve as source for isolating neural stem cells that can be further differentiated into OLP or oligodendrocyte using the subject methods.

For example, U.S. Pat. Nos. 6,235,527 and 6,900,054 describe the isolation of a glial precursor cell population, $A2B5^+$ $E\text{-}NCAM^-$ glial-restricted precursor (GRP) cells, from mammalian CNS, and the differentiation of these cells into oligodendrocytes, $A2B5^+$ process-bearing astrocytes, and $A2B5^-$ fibroblast-like astrocytes (but not into neurons). These GRP cells can be maintained by regeneration in culture. The GRP cells differ from oligodendrocyte-type-2 astrocyte (O-2A) progenitor cells in growth factor requirements, morphology, and progeny. Methods of use of GRP cells are also disclosed.

U.S. Pat. No. 6,897,061 describes a process for generating multipotent cells from glial cells using in vitro techniques to dedifferentiate fetal or adult mammalian glial cells into multipotent cells. The multipotent cells may further be differentiated into particular types of nervous system cells, including neurons, astrocytes, and oligodendrocytes. A small sample of astrocytes is used to establish an in vitro culture of cells that is expanded and processed to yield multipotent cells that may be used directly or be differentiated to yield neurons and/or oligodendrocytes and/or astrocytes. The invention includes implanting the generated cells into patients. The invention also includes a step of exposing the cells to a growth factor.

U.S. Pat. No. 6,673,606 describes differentiating a mesenchymal stromal cell to an oligodendrocyte precursor cell, comprises providing an in vitro composition comprising mesenchymal stromal cells and culturing the cells in neuroblastoma conditioned medium. Specifically, the method comprises: (i) providing a composition in vitro that consists essentially of the mesenchymal stromal cells and a physiologically compatible carrier, (ii) and culturing the cells in a medium comprising a neuroblastoma conditioned medium, wherein the culturing step provides oligodendrocyte precursor cells capable of differentiating into oligodendrocytes. The neuroblastoma conditioned medium may be B104 conditioned medium.

U.S. Pat. No. 6,361,996 describes multipotent neuroepithelial stem cells and lineage-restricted oligodendrocyte-astrocyte precursor cells. The neuroepithelial stem cells are capable of self-renewal and of differentiation into neurons, astrocytes, and oligodendrocytes. The oligodendrocyte-astrocyte precursor cells are derived from neuroepithelial stem cells, are capable of self-renewal, and can differentiate into oligodendrocytes and astrocytes, but not neurons. Methods of generating, isolating, and culturing such neuroepithelial stem cells and oligodendrocyte-astrocyte precursor cells are also disclosed.

U.S. Pat. No. 5,830,651 describes human cell lines having the characteristics of a pre-oligodendroglial stem cell which is essentially free of astrocyte and oligodendrocyte cell surface markers. One such pre-oligodendroglial stem cell line, HOP-1, is immortalized (see ATCC CRL 11881). The cells can be derived from neural tissue such as hippocampus, cerebellum, spinal cord, cortex, striatum, basal forebrain, ventral mesencephalon, and locus ceruleus.

Having obtained neural stem cells using any of the methods/sources described herein, the following subsection provides methods for (long-term) culturing of the neural stem cells.

B. In Vitro Proliferation of Neural Stem Cells

Cells can be obtained from donor tissue by dissociation of individual cells from the connecting extracellular matrix of the tissue. Tissue from a particular neural region is removed from the brain using a sterile procedure, and the cells are dissociated using any method known in the art, including treatment with enzymes such as trypsin, collagenase and the like, or by using physical methods of dissociation such as with a blunt instrument. Dissociation of fetal cells can be carried out in tissue culture medium, while a preferable medium for dissociation of juvenile and adult cells is low $Ca^{2+}$ artificial cerebral spinal fluid (aCSF). Regular aCSF contains 124 mM NaCl, 5 mM KCl, 1.3 mM $MgCl_2$, 2 mM $CaCl_2$, 26 mM $NaHCO_3$, and 10 mM D-glucose. Low $Ca^{2+}$ aCSF contains the same ingredients except for $MgCl_2$ at a concentration of 3.2 mM and $CaCl_2$ at a concentration of 0.1 mM. Dissociated cells are centrifuged at low speed, between 200 and 2000 rpm, usually between 400 and 800 rpm, and then resuspended in culture medium. The neural cells can be cultured in suspension or on a fixed substrate. However, substrates tend to induce differentiation of the neural stem cell progeny. Thus, suspension cultures are preferred if large numbers of undifferentiated neural stem cell progeny are desired. Cell suspensions are seeded in any receptacle capable of sustaining cells, particularly culture flasks, culture plates or roller bottles, and more particularly in small culture flasks such as 25 $cm^2$ culture flasks. Cells cultured in suspension are resuspended at approximately $5 \times 10^4$ to $2 \times 10^5$ cells/ml, preferably $1 \times 10^5$ cells/ml. Cells plated on a fixed substrate are plated at approximately $2-3 \times 10^3$ cells/$cm^2$, preferably $2.5 \times 10^3$ cells/$cm^2$.

The dissociated neural cells can be placed into any known culture medium capable of supporting cell growth, including HEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. However, a preferred embodiment for proliferation of neural stem cells is to use a defined, serum-free culture medium, as serum tends to induce differentiation and contains unknown components (i.e. is undefined). A defined culture medium is also preferred if the cells are to be used for transplantation purposes. A particularly preferable culture medium is a defined culture medium comprising a mixture of DMEM, F12, and a defined hormone and salt mixture. This culture medium is referred to herein as "Complete Medium."

An exemplary complete medium is a serum-free medium composed of DMEM/F-12 (1:1) including glucose (0.6%), glutamine (2 gM), sodium bicarbonate (3 mM), and HEPES (4-[2hydroxyethyl]-1-piperazineethanesulfonic acid) buffer (5 mM) (all from Sigma except glutamine [Gibco]). A defined hormone mix and salt mixture (Sigma) that included insulin (25 μg/ml), transferrin (100 μg/ml), progesterone (20 nM), putrescine (60 μM), and selenium chloride (30 nM) was used in place of serum. The complete medium is supplemented with 16-20 ng/ml EGF (purified from mouse sub-maxillary, Collaborative Research) or TGFα (human recombinant, Gibco). When using the complete medium, and after 10-14 days of in vitro culturing, the medium (DMEM only plus hormone mixture) and growth factors are replaced. This medium change is repeated every two to four days.

Conditions for culturing should be close to physiological conditions. The pH of the culture medium should be close to physiological pH, preferably between pH 6-8, more preferably between about pH 7 to 7.8, with pH 7.4 being most preferred. Physiological temperatures range between about 30° C. to 40° C. Cells are preferably cultured at temperatures between about 32° C. to about 38° C., and more preferably between about 35° C. to about 37° C.

The culture medium is supplemented with at least one proliferation-inducing growth factor. As used herein, the term "growth factor" refers to a protein, peptide or other molecule having a growth, proliferative, differentiative, or trophic effect on neural stem cells and/or neural stem cell progeny. Growth factors which may be used for inducing proliferation include any trophic factor that allows neural stem cells and precursor cells to proliferate, including any molecule which binds to a receptor on the surface of the cell to exert a trophic, or growth-inducing effect on the cell. Preferred proliferation-inducing growth factors include EGF, amphiregulin, acidic fibroblast growth factor (aFGF or FGF-1), basic fibroblast growth factor (bFGF or FGF-2), transforming growth factor alpha (TGFα), and combinations thereof. In a preferred embodiment, the growth factor is FGF-2.

Preferred proliferation-inducing growth factors include EGF and TGFα. A preferred combination of proliferation-inducing growth factors is EGF or TGFC with FGF-1 or FGF-2. Growth factors are usually added to the culture medium at concentrations ranging between about 1 fg/ml to 1 mg/ml. Concentrations between about 1 to 100 ng/ml are usually sufficient. Simple titration experiments can be easily performed to determine the optimal concentration of a particular growth factor.

In addition to proliferation-inducing growth factors, other growth factors may be added to the culture medium that influence proliferation and differentiation of the cells including NGF, platelet-derived growth factor (PDGF), thyrotropin releasing hormone (TRH), transforming growth factor betas (TGFβs), insulin-like growth factor (IGF-1) and the like.

Within 3-4 days in the presence of a proliferation-inducing growth factor, a multipotent neural stem cell begins to divide giving rise to a cluster of undifferentiated cells referred to herein as a "neurosphere." The cells of a single neurosphere are clonal in nature because they are the progeny of a single neural stem cell. In the continued presence of a proliferation-inducing growth factor such as EGF or the like, precursor cells within the neurosphere continue to divide resulting in an increase in the size of the neurosphere and the number of undifferentiated cells. The neurosphere is not immunoreactive for GFAP, neurofilament (NF), neuron-specific enolase (NSE) or myelin basic protein (MBP). However, precursor cells within the neurosphere are immunoreactive for nestin, an intermediate filament protein found in many types of undifferentiated CNS cells. The nestin marker was characterized by Lehndahl et al., Cell 60: 585-595, 1990. Antibodies are available to identify nestin, including the rat antibody referred to as Rat401. The mature phenotypes associated with the differentiated cell types that may be derived from the neural stem cell progeny are predominantly negative for the nestin phenotype.

After about 4 to 5 days in the absence of a substrate, the proliferating neurospheres lift off the floor of the culture dish and tend to form the free-floating clusters characteristic of neurospheres. It is possible to vary the culture conditions so that while the precursor cells still express the nestin phenotype, they do not form the characteristic neurospheres. The proliferating precursor cells of the neurosphere continue to proliferate in suspension. After about 3-10 days in vitro, and more particularly after about 6-7 days in vitro, the proliferating neurospheres are fed every 2-7 days, preferably every 2-4 days by gentle centrifugation and resuspension in Complete Medium containing a growth factor.

The neurospheres of the suspension culture can be easily passaged to reinitiate proliferation. After 6-7 days in vitro, the culture flasks are shaken well and the neurospheres allowed to settle on the bottom corner of the flask. The neurospheres are then transferred to a 50 ml centrifuge tube and centrifuged at low speed. The medium is aspirated, and the neurospheres are resuspended in a small amount of Complete Medium. Individual cells in the neurospheres can be separated by physical dissociation of the neurospheres with a blunt instrument, for example, by triturating the neurospheres with a pipette, especially a fire polished pasteur pipette, to form a single cell suspension of neural stem cell progeny. The cells are then counted and replated at the desired density to reinitiate proliferation. Single cells from the dissociated neuro-spheres are suspended in Complete Medium containing growth factor, and a percentage of these cells proliferate and form new neurospheres largely composed of undifferentiated cells. This procedure can be repeated weekly to result in a logarithmic increase in the number of viable cells at each passage. The procedure is continued until the desired number of precursor cells is obtained.

The number of neural stem cell progeny proliferated in vitro from the mammalian CNS can be increased dramatically by injecting a growth factor or combination of growth factors, for example EGF, FGF, or EGF and FGF together, into the ventricles of the donor in vivo using the in vivo proliferation methods described in more detail below. For example, about 6 days after infusion of EGF into the lateral ventricle of a mouse forebrain, the walls of the ventricle are removed and the stem cells harvested. Infusion of EGF into the lateral ventricle increases the efficiency of the yield of stem cells that proliferate to form neurospheres.

This ability to enhance the proliferation of neural stem cells proves invaluable when stem cells are to be harvested for later transplantation back into a patient, thereby making the initial surgery (1) less traumatic because less tissue would have to be removed, and (2) more efficient because a greater yield of stem cells per surgery would proliferate in vitro.

Additionally, the patient's stem cells, once having proliferated in vitro, could also be genetically modified in vitro using the techniques described below. The in vitro genetic modification may be more desirable in certain circumstances than in vivo genetic modification techniques when more control over the infection with the genetic material is required.

Neural stem cell progeny can be cryopreserved until they are needed by any method known in the art. The cells can be suspended in an isotonic solution, preferably a cell culture medium, containing a particular cryopreservant. Such cryopreservants include dimethyl sulfoxide (DMSO), glycerol and the like. These cryopreservants are used at a concentration of 5-15%, preferably 8-10%. Cells are frozen gradually to a temperature of $-10C$ to $-150°$ C., preferably $-20°$ C. to $-100°$ C., and more preferably $-70°$ C. to $-80°$ C.

C. Differentiation of Neural Stem Cell Progeny

The methods of the invention enhances the differentiation of the isolated and/or cultured neural stem cells to OLPs by inducing the co-expression of an Olig gene and a Nkx2.2 gene. Once the neural stem cells become OLPs, they may continue to develop along the oligodendrocyte lineage, or they may be further treated using the art-recognized methods for differentiation into mature oligodendrocytes. The methods described below may also be used in conjunction with the methods of the invention for differentiation of the neural stem cells to OLPs or ODCs.

Differentiation of the cells can be induced by any method known in the art which activates the cascade of biological events which lead to growth, which include the liberation of inositol triphosphate and intracellular $Ca^{2+}$, liberation of diacyl glycerol, and the activation of protein kinase C and other cellular kinases, and the like. Treatment with phorbol esters, differentiation-inducing growth factors and other chemical signals can induce differentiation. Differentiation can also be induced by plating the cells on a fixed substrate such as flasks, plates, or coverslips coated with an jonically charged surface such as poly-L-lysine and poly-L-ornithine and the like.

Other substrates may be used to induce differentiation such as collagen, fibronectin, laminin, MATRIGEL™ (Collaborative Research), and the like. Differentiation can also be induced by leaving the cells in suspension in the presence of a proliferation-inducing growth factor, without reinitiation of proliferation (i.e. without dissociating the neurospheres).

One method for inducing differentiation of the neural stem cell progeny comprises culturing the cells on a fixed substrate in a culture medium that is free of the proliferation-inducing growth factor. After removal of the proliferation-inducing growth factor, the cells adhere to the substrate (e.g. poly-ornithine-treated plastic or glass), flatten, and begin to differentiate into neurons and glial cells. At this stage the culture medium may contain serum such as 0.5-1.0% fetal bovine serum (FBS). However, for certain uses, if defined conditions are required, serum would not be used. Within 2-3 days, most or all of the neural stem cell progeny begin to lose immunoreactivity for nestin and begin to express antigens specific for oligodendrocytes as determined by immunocytochemistry techniques well known in the art.

Immunocytochemistry (e.g. dual-label immunofluorescence and immunoperoxidase methods) utilizes antibodies that detect cell proteins to distinguish the cellular characteristics or phenotypic properties of neurons from astrocytes and oligodendrocytes. In particular, cellular markers for neurons include NSE, NF, β-tub, MAP-2; and for glia, GFAP (an astrocyte marker), galactocerebroside (GalC) (a myelin glycolipid identifier of oligodendrocytes), and the like.

In situ hybridization histochemistry can also be performed, using cDNA or RNA probes specific for the oligodendrocyte peptide marker mRNAs. These techniques can be combined with immunocytochemical methods to enhance the identification of specific phenotypes. If necessary, the antibodies and molecular probes discussed above can be applied to Western and Northern blot procedures respectively to aid in cell identification.

Cells that do not express intermediate filaments specific for neurons or for astrocytes, begin to express markers specific for oligodendrocytes in a correct temporal fashion. That is, the cells first become immunoreactive for O4, galactocerebroside (GalC, a myelin glycolipid) and finally, MBP. These cells also possess a characteristic oligodendrocyte morphology.

Exogenous growth factors can be added alone or in various combinations. They can also be added in a temporal sequence (i.e. exposure to a first growth factor influences the expression of a second growth factor receptor, Neuron 4:189-201 (1990). Among the growth factors and other molecules that can be used to influence the differentiation of precursor cells in vitro are FGF-1, FGF-2, ciliary neurotrophic factor (CNTF), NGF, brain-derived neurotrophic factor (BDNF), neurotrophin 3, neurotrophin 4, interleukins, leukemia inhibitory factor (LIF), cyclic adenosine monophosphate, forskolin, tetanus toxin, high levels of potassium, amphiregulin, TGF-α, TGF-β, insulin-like growth factors, dexamethasone (glucocorticoid hormone), isobutyl 3-methylxanthine, somatostatin, growth hormone, retinoic acid, and PDGF.

D. Genetic Modification of Neural Stem Cell Progeny

According to the instant invention, the neural stem cells can be induced to co-express an Olig gene and an Nkx2.2 gene to enhance the differentiation into OLPs or oligodendrocytes.

In one embodiment, exogenous genes, such as an Olig gene and/or an Nkx2.2 gene may need to be introduced into the neural stem cells to achieve co-expression. Such Olig genes and/or Nkx2.2 genes may be under the control of identical or different constitutive or inducible promoters to effect optimal co-expression.

In other embodiments, inhibitors or antagonists of endogenous Olig genes or Nkx2.2 genes may themselves be inhibited/antagonized, to induce the expression of endogenous Olig genes or Nkx2.2 genes. For example, members of the inhibitor of differentiation (ID) family of HLH transcriptional inhibitors, such as the ID2 and ID4 proteins, may bind the Olig proteins and inhibit their function. Thus antagonists of the id genes, such as siRNA (or various derivatives thereof), ribozymes, antibodies, antisense polynucleotides, and other specific inhibitors of these genes/proteins may be used to relieve their inhibition on endogenous Olig/Nkx2.2 expression.

Although the precursor cells are non-transformed primary cells, they possess features of a continuous cell line. In the undifferentiated state, in the presence of a proliferation-inducing growth factor such as EGF, the cells continuously divide and are therefore excellent targets for genetic modification. The term "genetic modification" as used herein refers to the stable or transient alteration of the genotype of a precursor cell by intentional introduction of exogenous DNA. "DNA" as used herein may be synthetic, or naturally derived, and may contain genes, portions of genes, or other useful DNA sequences (such as heterologous promoters, enhancers, translation/transcription termination signals, etc.). The term "genetic modification" as used herein is not meant to include naturally occurring alterations such as that which occurs through natural viral activity, natural genetic recombination, or the like.

Exogenous DNA such as the Olig genes and the Nkx2.2 genes, may be introduced to a precursor cell by viral vectors (retrovirus, modified herpes viral, herpes-viral, adenovirus, adeno-associated virus, and the like) or direct DNA transfection (lipofection, $CaPO_4$ transfection, DEAE-dextran, electroporation, and the like). The genetically modified cells of the present invention possess the added advantage of having the capacity to fully differentiate to produce neurons or macroglial cells in a reproducible fashion using a number of differentiation protocols.

In another embodiment, the precursor cells may be derived from transgenic animals, such as transgenic rodents with the Olig genes and the Nkx2.2 genes under the control of constitutive or inducible promoters, and thus are in a sense already genetically modified. There are several methods presently used for generating transgenic animals. The technique used most often is direct microinjection of DNA into single-celled fertilized eggs. Other techniques include retroviral-mediated transfer, or gene transfer in embryonic stem cells. These techniques and others are detailed by Hogan et al. in Manipulating the Mouse Embryo, A Laboratory Manual (Cold Spring Harbor Laboratory Ed., 1986). Use of these transgenic animals has certain advantages including the fact that there is no need to transfect healthy neurospheres. Precursor cells derived from transgenic animals will exhibit stable gene expression. Using transgenic animals, it is possible to breed in new genetic combinations, such as by breeding in additional genes helpful for oligodendrocyte lineage differentiation. The transgenic animal may have integrated into its genome any useful gene that is expressed by neural cells. Examples of useful DNA are given below in the discussion of genetically modifying precursor cells.

A significant challenge for cellular transplantation in the CNS is the identification of the donor cells after implantation within the host. A number of strategies have been employed to mark donor cells, including tritiated labels, fluorescent dyes, dextrans, and viral vectors carrying reporter genes. However, these methods suffer from inherent problems of toxicity, stability, or dilution over the long term. The use of neural cells derived from transgenic animals may provide an improved means by which identification of transplanted neural cells can be achieved. A transgenic marking system provides a more stable and efficient method for cell labeling. In this system, promoter elements, for example for GFAP and MBP, can direct the expression of the E. coli β-galactosidase reporter gene in transgenic mice. In these systems, cell-specific expression of the reporter gene occurs in astrocytes (GFAP-lacZ) and in oligodendrocytes (MBP-lacZ) in a developmentally-regulated manner.

Once propagated, the neurosphere cells are mechanically dissociated into a single cell suspension and plated on petri dishes in a medium where they are allowed to attach overnight. The precursor cells are then genetically modified. If the precursor cells are generated from transgenic animals, then they may or may not be subjected to further genetic modification, depending upon the properties desired of the cells. Any useful genetic modification of the cells is within the scope of the present invention.

The genetic modification is performed either by infection with recombinant retroviruses or transfection using methods known in the art (see Maniatis et al., in Molecular Cloning: A Laboratory Manual, Cold Spring Harbor Laboratory, N.Y. (1982)). Briefly, the chimeric gene constructs will contain viral, for example retroviral long terminal repeat (LTR), simian virus 40 (SV40), cytomegalovirus (CMV); or mammalian cell-specific promoters such as tyrosine hydroxylase (TH, a marker for dopamine cells), DBH, phenylethanolamine N-methyltransferase (PNMT), ChAT, GFAP, NSE, the NF proteins (NF-L, NF-M, NF-H, and the like) that direct the expression of the structural genes encoding the desired protein. In addition, the vectors will include a drug selection marker, such as the E. coli aminoglycoside phosphotransferase gene, which when coinfected with the experimental gene confers resistance to geneticin (G418), a protein synthesis inhibitor.

After successfully transfected/infected cells are selected, they can be cloned using limiting dilution in 96 multi-well plates and assayed for the presence of the desired biologically active substance. Clones that express high levels of the desired substance are grown and their numbers expanded in T-flasks. The specific cell line can then be cyropreserved. Multiple clones of genetically modified precursor cells will be obtained. Some may give rise preferentially to neuronal cells, and some to glial cells.

The genetically modified precursor cells can be implanted for cell/gene therapy into the CNS of a recipient in need of the biologically active molecule produced by the genetically modified cells. Transplantation techniques are detailed below.

In certain embodiments, the genetically modified precursor cells can be subjected to various differentiation protocols in vitro prior to implantation. For example, genetically modified precursor cells may be removed from the culture medium which allows proliferation and differentiated using any of the protocols described above. The protocol used will depend upon the type of genetically modified cell desired. Once the cells have differentiated, they are again assayed for expression of the desired protein (see above for oligodendrocyte markers). Cells having the desired phenotype can be isolated and implanted into recipients in need of the protein or biologically active molecule that is expressed by the genetically modified cell.

In other embodiments, the Olig proteins and/or the Nkx2.2 proteins may be provided directly in vivo to the target cells (e.g., the neural stem cells in the ventricular zone), and the uptake of these proteins may be facilitated by fusing these proteins with certain so-called transcytosis peptides.

Specifically, the subject Olig and Nkx2.2 proteins can be provided as fusion peptide along with a second peptide which promotes "transcytosis," e.g., uptake of the peptide by epithelial cells and other cell types. To illustrate, the subject Olig and Nkx2.2 proteins can be provided as part of a fusion polypeptide with all or a fragment of the N-terminal domain of the HIV protein Tat, e.g., residues 1-72 of Tat or a smaller fragment thereof, which can promote transcytosis. In other embodiments, the subject Olig and Nkx2.2 proteins can be provided as fusion polypeptide with all or a portion of the antenopedia III protein.

To further illustrate, the subject Olig and Nkx2.2 proteins (or peptidomimetic) can be provided as a chimeric peptide which includes a heterologous peptide sequence ("internalizing peptide") which drives the translocation of an extracellular form of a subject Olig and Nkx2.2 protein sequence across a cell membrane in order to facilitate intracellular localization of these proteins. In this regard, the therapeutic polypeptide sequence is one which is active intracellularly. The internalizing peptide, by itself, is capable of crossing a cellular membrane by, e.g., transcytosis, at a relatively high rate. The internalizing peptide is conjugated, e.g., as a fusion protein, to the subject polypeptides. The resulting chimeric peptide is transported into cells at a higher rate relative to the activator polypeptide alone to thereby provide an means for enhancing its introduction into cells to which it is applied, e.g., to enhance topical applications of the subject Olig and Nkx2.2 proteins.

In one embodiment, the internalizing peptide is derived from the *Drosophila* antennapedia protein, or homologs thereof. The 60 amino acid long homeodomain of the homeoprotein antennapedia has been demonstrated to translocate through biological membranes and can facilitate the translocation of heterologous polypeptides to which it is couples. See for example Derossi et al. (1994) *J Biol Chem* 269:10444-10450; and Perez et al. (1992) *J Cell Sci* 102: 717-722. Recently, it has been demonstrated that fragments as small as 16 amino acids long of this protein are sufficient to drive internalization. See Derossi et al. (1996) *J Biol Chem* 271: 18188-18193.

The present invention contemplates an Olig or Nkx2.2 polypeptide (or peptidomimetic) sequence as described herein, and at least a portion of the Antennapedia protein (or homolog thereof) sufficient to increase the transmembrane transport of the chimeric protein, relative to the Olig or Nkx2.2 polypeptide or peptidomimetic, by a statistically significant amount.

Another example of an internalizing peptide is the HIV transactivator (TAT) protein. This protein appears to be divided into four domains (Kuppuswamy et al. (1989) *Nucl. Acids Res.* 17: 3551-3561). Purified TAT protein is taken up by cells in tissue culture (Frankel and Pabo, (1989) *Cell* 55: 1189-1193), and peptides, such as the fragment corresponding to residues 37-62 of TAT, are rapidly taken up by cell in vitro (Green and Loewenstein, (1989) *Cell* 55: 1179-1188). The highly basic region mediates internalization and targeting of the internalizing moiety to the nucleus (Ruben et al., (1989) *J. Virol.* 63: 1-8).

Another exemplary transcellular polypeptide can be generated to include a sufficient portion of mastoparan (T. Higashijima et al., (1990) *J. Biol. Chem.* 265: 14176) to increase the transmembrane transport of the chimeric protein.

While not wishing to be bound by any particular theory, it is noted that hydrophilic polypeptides may also be physiologically transported across the membrane barriers by coupling or conjugating the polypeptide to a transportable peptide which is capable of crossing the membrane by receptor-mediated transcytosis. Suitable internalizing peptides of this type can be generated using all or a portion of, e.g., a histone, insulin, transferrin, basic albumin, prolactin and insulin-like growth factor I (IGF-I), insulin-like growth factor II (IGF-II) or other growth factors. For instance, it has been found that an insulin fragment, showing affinity for the insulin receptor on capillary cells, and being less effective than insulin in blood sugar reduction, is capable of transmembrane transport by receptor-mediated transcytosis and can therefor serve as an internalizing peptide for the subject transcellular peptides and peptidomimetics. Preferred growth factor-derived internalizing peptides include EGF (epidermal growth factor)-derived peptides, such as CMHIESLDSYTC (SEQ ID NO: 1) and CMYIEALDKYAC (SEQ ID NO: 2); TGF-beta (transforming growth factor beta)-derived peptides; peptides derived from PDGF (platelet-derived growth factor) or PDGF-2; peptides derived from IGF-I (insulin-like growth factor) or IGF-II; and FGF (fibroblast growth factor)-derived peptides. These peptides may be useful since the neural stem cells are responsive to many growth factors, by virtue of having cells surface receptors for these growth factors.

Another class of translocating/internalizing peptides exhibits pH-dependent membrane binding. For an internalizing peptide that assumes a helical conformation at an acidic pH, the internalizing peptide acquires the property of amphiphilicity, e.g., it has both hydrophobic and hydrophilic interfaces. More specifically, within a pH range of approximately 5.0-5.5, an internalizing peptide forms an alpha-helical, amphiphilic structure that facilitates insertion of the moiety into a target membrane. An alpha-helix-inducing acidic pH environment may be found, for example, in the low pH environment present within cellular endosomes. Such internalizing peptides can be used to facilitate transport of the subject peptides and peptidomimetics, taken up by an endocytic mechanism, from endosomal compartments to the cytoplasm.

A preferred pH-dependent membrane-binding internalizing peptide includes a high percentage of helix-forming residues, such as glutamate, methionine, alanine and leucine. In addition, a preferred internalizing peptide sequence includes ionizable residues having pKa's within the range of pH 5-7, so that a sufficient uncharged membrane-binding domain will be present within the peptide at pH 5 to allow insertion into the target cell membrane.

A particularly preferred pH-dependent membrane-binding internalizing peptide in this regard is Xaa1-Xaa2-Xaa3-EAALA(EALA)4-EALEALAA-amide (SEQ ID NO: 3), which represents a modification of the peptide sequence of Subbarao et al. (*Biochemistry* 26: 2964, 1987). Within this peptide sequence, the first amino acid residue (Xaa1) is preferably a unique residue, such as cysteine or lysine, that facilitates chemical conjugation of the internalizing peptide to a targeting protein conjugate. Amino acid residues 2-3 may be selected to modulate the affinity of the internalizing peptide for different membranes. For instance, if both residues 2 and 3 are Lys or Arg, the internalizing peptide will have the capacity to bind to membranes or patches of lipids having a negative surface charge. If residues 2-3 are neutral amino acids, the internalizing peptide will insert into neutral membranes.

Yet other preferred internalizing peptides include peptides of apo-lipoprotein A-1 and B; peptide toxins, such as melittin, bombolittin, delta hemolysin and the pardaxins; antibiotic peptides, such as alamethicin; peptide hormones, such as calcitonin, corticotrophin releasing factor, beta endorphin, glucagon, parathyroid hormone, pancreatic polypeptide; and peptides corresponding to signal sequences of numerous secreted proteins. In addition, exemplary internalizing peptides may be modified through attachment of substituents that enhance the alpha-helical character of the internalizing peptide at acidic pH.

Yet another class of internalizing peptides suitable for use within the present invention include hydrophobic domains that are "hidden" at physiological pH, but are exposed in the low pH environment of the target cell endosome. Upon pH-induced unfolding and exposure of the hydrophobic domain, the moiety binds to lipid bilayers and effects translocation of the covalently linked polypeptide into the cell cytoplasm. Such internalizing peptides may be modeled after sequences identified in, e.g., *Pseudomonas* exotoxin A, clathrin, or Diphtheria toxin.

Pore-forming proteins or peptides may also serve as internalizing peptides herein. Pore-forming proteins or peptides may be obtained or derived from, for example, C9 complement protein, cytolytic T-cell molecules or NK-cell molecules. These moieties are capable of forming ring-like structures in membranes, thereby allowing transport of attached polypeptide through the membrane and into the cell interior.

Mere membrane intercalation of an internalizing peptide may be sufficient for translocation of the subject polypeptide or peptidomimetic, across cell membranes. However, translocation may be improved by attaching to the internalizing peptide a substrate for intracellular enzymes (i.e., an "accessory peptide"). It is preferred that an accessory peptide be attached to a portion(s) of the internalizing peptide that protrudes through the cell membrane to the cytoplasmic face. The accessory peptide may be advantageously attached to one terminus of a translocating/internalizing moiety or anchoring peptide. An accessory moiety of the present invention may contain one or more amino acid residues. In one embodiment, an accessory moiety may provide a substrate for cellular phosphorylation (for instance, the accessory peptide may contain a tyrosine residue).

An exemplary accessory moiety in this regard would be a peptide substrate for N-myristoyl transferase, such as GNAAAARR (SEQ ID NO: 4, Eubanks et al., in: *Peptides. Chemistry and Biology*, Garland Marshall (ed.), ESCOM, Leiden, 1988, pp. 566-69). In this construct, an internalizing peptide would be attached to the C-terminus of the accessory peptide, since the N-terminal glycine is critical for the accessory moiety's activity. This hybrid peptide, upon attachment to an E2 peptide or peptidomimetic at its C-terminus, is N-myristylated and further anchored to the target cell membrane, e.g., it serves to increase the local concentration of the peptide at the cell membrane.

Suitable accessory peptides include peptides that are kinase substrates, peptides that possess a single positive charge, and peptides that contain sequences which are glycosylated by membrane-bound glycotransferases. Accessory peptides that are glycosylated by membrane-bound glycotransferases may include the sequence x-NLT-x, where "x" may be another peptide, an amino acid, coupling agent or hydrophobic molecule, for example. When this hydrophobic tripeptide is incubated with microsomal vesicles, it crosses vesicular membranes, is glycosylated on the luminal side, and is entrapped within the vesicles due to its hydrophilicity (C. Hirschberg et al., (1987) *Ann. Rev. Biochem.* 56: 63-87). Accessory peptides that contain the sequence x-NLT-x thus will enhance target cell retention of corresponding polypeptide.

In another embodiment of this aspect of the invention, an accessory peptide can be used to enhance interaction of the subject polypeptide or peptidomimetic with the target cell. Exemplary accessory peptides in this regard include peptides derived from cell adhesion proteins containing the sequence "RGD", or peptides derived from laminin containing the sequence CDPGYIGSRC (SEQ ID NO: 5). Extracellular matrix glycoproteins, such as fibronectin and laminin, bind to cell surfaces through receptor-mediated processes. A tripeptide sequence, RGD, has been identified as necessary for binding to cell surface receptors. This sequence is present in fibronectin, vitronectin, C3bi of complement, von-Willebrand factor, EGF receptor, transforming growth factor beta, collagen type I, lambda receptor of *E. coli*, fibrinogen and Sindbis coat protein (E. Ruoslahti, *Ann. Rev. Biochem.* 57: 375-413, 1988). Cell surface receptors that recognize RGD sequences have been grouped into a superfamily of related proteins designated "integrins." Binding of "RGD peptides" to cell surface integrins will promote cell-surface retention, and ultimately translocation, of the polypeptide.

As described above, the internalizing and accessory peptides can each, independently, be added to the subject polypeptide or peptidomimetic by either chemical cross-linking or in the form of a fusion protein. In the instance of fusion proteins, unstructured polypeptide linkers can be included between each of the peptide moieties.

In an exemplary embodiment, a subject polypeptide or peptidomimetic is engineered to include an integrin-binding RGD peptide/SV40 nuclear localization signal (see, for example Hart S L et al., 1994*; J. Biol. Chem.* 269: 12468-12474), such as encoded by the nucleotide sequence provided in the Nde1-EcoR1 fragment: CATATGGUTGACTGCCGTGGCGAT ATGTTCGGTTGCGGTGCTCCTCCAAAAAAGAAGAGAAAGGTAGCTGGATTC (SEQ ID NO: 6), which encodes the RGD/SV40 nucleotide sequence: MGGCRGDMFGCGAPPKKKRKVAGF (SEQ ID NO: 7).

In another embodiment, the protein can be engineered with the HIV-1 tat(1-72) polypeptide, e.g., as provided by the Nde1-EcoR1 fragment: CATATGGAGCCAGTAGATCCTAGACTAGAGCCCTGGAAGCATCCAG- GAAGTCAGCC TAAAACTGCTTGTACCAATTGCTAT-
TGTAAAAAGTGTTGCTTTCATTGCCAAGTGTTT
CATAACAAAAGCCCTTGGCATCTC-
CTATGGCAGGAAGAAGCGAGACAGCGACGAAG
ACCTCCTCAAGGCAGTCAGACTCAT-
CAAGTTTCTCTAAGTAAGCAAGGATTC (SEQ ID NO:
8), which encodes the HIV-1 tat(1-72) peptide sequence:
MEPVDPRLEPWKHPGSQPKTACTNCYCK-
KCCFHCQVCFITKALGISYGRKKRRQRRRPP
QGSQTHQVSLSKQ (SEQ ID NO: 9). In still another
embodiment, the fusion protein includes the HSV-1 VP22
polypeptide (Elliott G., O'Hare P (1997) *Cell* 88: 223-233)
provided by the Nde1-EcoR1 fragment:

(SEQ ID NO: 10)
CATATGACCTCTCGCCGCTCCGTGAAGTCGGGTCCGCGGGAGGTTCCGCG

CGATGAGTACGAGGATCTGTACTACACCCCGTCTTCAGGTATGGGCAGTC

CCGATAGTCCGCCTGACACCTCCCGCCGTGGCGCCCTACAGACACGCTCG

CGCCAGAGGGGCGAGGTCCGTTTCGTCCAGTACGACGAGTCGGATTATGC

CCTCTACGGGGCTCGTCATCCGAAGACGACGAACACCCGGAGGTCCCCC

GGACGCGGCGTCCCGTTTCCGGGGCGGTTTTGTCCGGCCCGGGGCCTGCG

CGGGCGCCTCCGCCACCCGCTGGGTCCGGAGGGGCCGGACGCACACCCAC

CACCGCCCCCGGGCCCCCCGAACCCAGCGGGTGGCGACTAAGGCCCCCG

CGGCCCCGGCGGCGGAGACCACCCGCGGCAGGAAATCGGCCCAGCCAGAA

TCCGGCGGACTCCCAGACGCCCCCGCGTCGACGGCGCCAACCCGATCCAA

GACACCCGCGCAGGCGCTGGCCAGAAAGGTGCACTTTAGCACCGCCCCCC

CAAACCCCGACGCGCCATGGACCCCCCGGGTGGCCGGCTTTAACAAGCGC

GTCTTCTGCGCCGCGGTCGGGCGCCTGGCGGCCATGCATGCCCGGATGGC

GGCGGTCCAGCTCTGGGACATGTCGCGTCCGCGCACAGACGAAGACCTCA

ACGAACTCCTTGGCATCACCACCATCCGCGTGACGGTCTGCGAGGGCAAA

AACCTGCTTCAGCGCGCCAACGAGTTGGTGAATCCAGACGTGGTGCAGGA

CGTCGACGCGGCCACGGCGACTCGAGGGCGTTCTGCGGCGTCGCGCCCCA

CCGAGCGACCTCGAGCCCCAGCCCGCTCCGCTTCTCGCCCCAGACGGCCC

GTCGAGGAATTC which encodes the HSV-1 VP22 peptide having the sequence:

(SEQ ID NO: 11)
MTSRRSVKSGPREVPRDEYEDLYYTPSSGMASPDSPPDTSRRGALQTRSR

QRGEVRFVQYDESDYALYGGSSSEDDEHPEVPRTRRPVSGAVLSGPGPAR

APPPPAGSGGAGRTPTTAPRAPRTGRVATKAPAAPAAETTRGRKSAQPES

AALPDAPASTAPTRSKTPAQGLARKLHFSTAPPNPDAPWTPRVAGFNKRV

FCAAVGRLAAMHARMAAVQLWDMSRPRTDEDLNELLGITTIRVTVCEGKN

LLQRANELVNPDVVQDVDAATATRGRSAASRPTERPRAPARSASRPRRPV

E.

In still another embodiment, the fusion protein includes the C-terminal domain of the VP22 protein from, e.g., the nucleotide sequence (Nde1-EcoR1 fragment):

(SEQ ID NO: 12)
CATATGGACGTCGACGCGGCCACGGCGACTCGAGGGCGTTCTGCGGCGTC

GCGCCCCACCGAGCGACCTCGAGCCCCAGCCCGCTCCGCTTCTCGCCCCA

GACGGCCCGTCGAGGAATTC.

which encodes the VP22 (C-terminal domain) peptide sequence:

(SEQ ID NO: 13)
MDVDAATATRGRSAASRPTERPRAPARSASRPRRPVE.

In certain instances, it may also be desirable to include a nuclear localization signal as part of the subject polypeptide to enhance their localization to the nucleus once internalized. All peptide constructs are preferably checked for having retained the desired biological functions.

In the generation of fusion polypeptides including the subject polypeptides, it may be necessary to include unstructured linkers in order to ensure proper folding of the various peptide domains. Many synthetic and natural linkers are known in the art and can be adapted for use in the present invention, including the (Gly3Ser)$_4$ (SEQ ID NO: 14) linker or the like.

E. Oilg Genes and Nkx2.2 Genes

"Olig genes" or "Olig polynucleotides encoding function Olig proteins (including full-length, partial sequence, fusions, NLS tagged version, etc.) are known in the art.

For example, human Oilg genes are described in NCBI's RefSeq database as NM__138983 (Oilg1), NM__005806 (Oilg2), and NM__175747 (Olig3). The corresponding protein sequences are NP__620450 (Olig1), NP__005797 (Olig2), and NP__786923 (Olig3).

Other sequences or partial sequences, their derivatives (such as changing the wobble nucleotide without changing the encoded amino acid sequence, or making conservative changes in the amino acid sequences) can be readily obtained by standard sequence homolog searches in public/private databases, using such sequences as query.

Merely to illustrate, some of the related Oilg protein sequences are listed below:

BAE87579 and BAE91283 (*Macaca fascicularis*), NP__058663 (*Mus musculus*); XP__221668 (rat); AAF61722 (*Mus musculus*); NP__001026697 (chicken); XP__588802 (*Bos taurus*); BAD93028 (*Homo sapiens*); XP__852212 (*Canis familiaris*); XP__586373 (*Bos taurus*); NP__068538 (*Rattus norvegicus*); NP__058664 (*Mus musculus*); BAE34667 (*Mus musculus*); XP__527513 (*Pan troglodytes*); XP__610701 (*Bos taurus*); XP__541122 (*Canis familiaris*); XP__218772 (*Rattus norvegicus*); AAH57564 and NP__443734 (*Mus musculus*); etc.

Human Nkx2.2 gene is described in NCBI's RefSeq database as NM__002509. The corresponding protein sequence is NP__002500. Other related sequences include: XP__542867 (*Canis familiaris*); XP__345447 (*Rattus norvegicus*); NP__035049 & AAF44652 & AAK93795 (*Mus musculus*); XP__610195 (*Bos taurus*); CAA57165 (*Mesocricetus auratus*); AAY46193 (*Ovis aries*); XP__525279 (*Pan troglodytes*); BAC65247 (*Oryzias latipes*); AAW59439 (*Macaca fascicularis*); AAG16976 (*Homo sapiens*); etc.

Human Nkx2.5 gene is described in NCBI's RefSeq database as NM__004387.2. The corresponding protein sequence is NP__004378. Other related sequences include: XP__583382.1 (*Bos taurus*); NP__001010959.1 (*Canis famil-* iaris); NP_032726.1 (*Mus musculus*); NP_446103.1 (*Rattus norvegicus*); XP_518104.1 (*Pan troglodytes*), etc.

All these sequences, especially those originating from mammalian species or closely related species in evolution, are within the scope of the invention.

The subject Olig and Nkx2.2 polypeptides also include those at least about 80%, 85%, 90%, 95%, 96%, 97%, 98%, 99%, or nearly 100% identical to any of the human Olig1, Olig2, or Olig3 proteins, or Nkx2.2 protein, respectively.

The subject Oilg and Nkx2.2 polynucleotides also include those that can hybridize under stringent hybridization conditions. Stringent hybridization conditions include those equivalent to about 20-27° C. below the melting temperature ($T_m$) of the DNA duplex formed in about 1 M salt. Many equivalent procedures/protocols exist in the art, and several popular molecular cloning manuals describe suitable conditions for stringent hybridization and, furthermore, provide formulas for calculating the length of hybrids expected to be stable under these conditions (see e.g. *Current Protocols in Molecular Biology*, John Wiley & Sons, N.Y. (1989), 6.3.1-6 or 13.3.6; or pp. 9.47-9.57 of Sambrook, et al. (1989) *Molecular Cloning,* 2nd ed., CSH Press).

F. In Vivo Proliferation, Differentiation, and Genetic Modification of Neural Stem Cell Progeny Neural stem cells and their progeny can be induced to proliferate and differentiate in vivo by administering to the host, any growth factor(s) or pharmaceutical composition that will induce proliferation and/or differentiation of the cells. Thus after the transplantation of the subject OLP or ODC cells, procedures described below may be used to further proliferate/differentiate the transplanted OLP or ODC cells.

The growth factors that can be used for this purpose include any growth factor known in the art, including the growth factors described above for in vitro proliferation and differentiation. Pharmaceutical compositions include any substance that blocks the inhibitory influence and/or stimulates neural stem cells and stem cell progeny to proliferate and ultimately differentiate.

In addition, the techniques described above to proliferate, differentiate, and genetically modify neural stem cells in vitro can be adapted to in vivo techniques, to achieve similar results. Such in vivo manipulation and modification of these cells allows cells lost, due to injury or disease, to be endogenously replaced, thus obviating the need for transplanting foreign cells into a patient. Additionally, the cells can be modified or genetically engineered in vivo so that they express the subject Olig gene and Nkx2.2 gene for enhanced differentiation into OLPs and oligodendrocytes in the treatment of neurological disorders.

Administration of growth factors can be done by any method, including injection cannula, transfection of cells with growth hormone-expressing vectors, injection, timed-release apparati which can administer substances at the desired site, and the like. Pharmaceutical compositions can be administered by any method, including injection cannula, injection, oral administration, timed-release apparati and the like. The neural stem cells can be induced to proliferate and differentiate in vivo by induction with particular growth factors or pharmaceutical compositions which will induce their proliferation and differentiation. Therefore, this latter method circumvents the problems associated with transplantation and immune reactions to foreign cells. Any growth factor can be used, particularly EGF, TGFα, FGF-1, FGF-2 and NGF.

Growth factors can be administered in any manner known in the art in which the factors may either pass through or by-pass the blood-brain barrier. Methods for allowing factors to pass through the blood-brain barrier include minimizing the size of the factor, or providing hydrophobic factors which may pass through more easily.

The fact that neural stem cells are located in the tissues lining ventricles of mature brains offers several advantages for the modification and manipulation of these cells in vivo and the ultimate treatment of various neurological diseases, disorders, and injury that affect different regions of the CNS. Therapy for these can be tailored accordingly so that stem cells surrounding ventricles near the affected region would be manipulated or modified in vivo using the methods described herein.

The ventricular system is found in nearly all brain regions and thus allows easier access to the affected areas. If one wants to modify the stem cells in vivo by exposing them to a composition comprising a growth factor or a viral vector, it is relatively easy to implant a device that administers the composition to the ventricle and thus, to the neural stem cells. For example, a cannula attached to an osmotic pump may be used to deliver the composition. Alternatively, the composition may be injected directly into the ventricles. The neural stem cell progeny can migrate into regions that have been damaged as a result of injury or disease. Furthermore, the close proximity of the ventricles to many brain regions would allow for the diffusion of a secreted neurological agent by the stem cells or their progeny.

For the treatment of MS and other demyelinating or hypomyelinating disorders, and for the treatment of Amyotrophic Lateral Sclerosis or other motor neuron diseases, growth factors and/or viral vectors capable of directing the expression of the subject Olig gene and Nkx2.2 gene would be delivered to the central canal.

In addition to treating CNS tissue immediately surrounding a ventricle, a viral vector, DNA, growth factor, or other neurological agent can be easily administered to the lumbar cistern for circulation throughout the CNS.

Under normal conditions subependymal precursors do not differentiate or migrate, rather, their fate appears to be cell death after an undefined number of cell divisions (Morshead and Van der Kooy, supra). This explanation is also supported by PCR evidence. Injection of growth factors into the lateral ventricle alters this fate. In addition, retroviruses have been injected into the lateral ventricles for six consecutive days. Implanting cannulae attached to EGF-filled osmotic pumps into the lateral ventricles on the same day as (and 1 or 6 days following) retrovirus injection results in an increase in the total number of RV-β-gal labeled cells 6 days later (from an average of 20 cells/brain to 150 cells/brain).

It is known from the PCR experiments described above that 6 days following retroviral injection no cells exist that contain non-expressed retroviral DNA. Thus these results indicate that the EGF-induced increase in β-gal positive cell number is due to the expansion of the clone size of the retrovirally labeled constitutively proliferative population. It is also possible that part of this increase is due to the activation by EGF of a relatively quiescent stem cell.

Interestingly, this expansion of the number of β-gal labeled cells is accompanied by the migration of these cells away from the subependymal medially, laterally, rostrally, and caudally with subsequent differentiation. Thus, infusion of EGF or similar growth factors induces the proliferation, migration and differentiation of neural stem cells and progenitor cells in vivo, and can be used therapeutically to replace neural cells lost due to injury or disease. In a preferred embodiment EGF and FGF are administered together or sequentially.

The normal fate of the constitutively proliferating cell population (i.e. cell death) can be altered by administering Bcl-2 or genetically modifying the cells with the bcl-2 gene. The gene product is known to prevent programmed cell death (apoptosis) in a variety of cell types. Similar to the EGF experiments, a clonal expansion of the constitutively proliferating cell population is achieved following infection with bcl-2.

Other ways of passing the blood-brain barrier include in vivo transfection of neural stem cells and stem cell progeny with expression vectors containing genes that code for the subject Olig genes and/or Nkx2.2 gene, or certain growth factors, etc., so that the cells themselves produce these proteins. Any useful genetic modification of the cells is within the scope of the present invention. For example, in addition to genetic modification of the cells to express exogenous Olig genes and/or Nkx2.2 genes, the cells may be modified to express other growth factors effective for stimulating OLP/ODC proliferation/differentiation.

Preferably, the genetic modification is performed either by infection of the cells lining ventricular regions with recombinant retroviruses or transfection using methods known in the art including $CaPO_4$ transfection, DEAE-dextran transfection, polybrene transfection, by protoplast fusion, electroporation, lipofection, and the like [see Maniatis et al., supra]. Any method of genetic modification, now known or later developed can be used. With direct DNA transfection, cells could be modified by particle bombardment, receptor mediated delivery, and cationic liposomes. When chimeric gene constructs are used, they generally will contain viral, for example retroviral long terminal repeat (LTR), simian virus 40 (SV40), cytomegalovirus (CMV); or mammalian cell-specific promoters such as those for TH, DBH, phenylethanolamine N-methyltransferase, ChAT, GFAP, NSE, the NF proteins (NF-L, NF-M, NF-H, and the like) that direct the expression of the structural genes encoding the desired protein.

If a retroviral construct is to be used to genetically modify normally quiescent stem cells, then it is preferable to induce the proliferation of these cells using the methods described herein. For example, an osmotic infusion pump could be used to deliver growth factors to the central canal several days prior to infection with the retrovirus. This assures that there will be actively dividing neural stem cells which are susceptible to infection with the retrovirus.

When the genetic modification is for the production of a biologically active substance, the substance will generally be one that is useful for the treatment of a given CNS disorder. For example, according to the instant invention, neural stem cells may be genetically modify to express endogenous or exogenous Olig genes and/or Nkx2.2 genes.

Any expression vector known in the art can be used to express the growth factor, as long as it has a promoter which is active in the cell, and appropriate termination and polyadenylation signals. These expression vectors include recombinant vaccinia virus vectors including pSC11, or vectors derived various viruses such as from Simian Virus 40 (SV40, i.e. pSV2-dhfr, pSV2neo, pko-neo, pSV2gpt, pSVT7 and pBABY), from Rous Sarcoma Virus (RSV, i.e. pRSVneo), from mouse mammary tumor virus (MMTV, i.e. pMSG), from adenovirus (pMT2), from herpes simplex virus (HSV, i.e. pTK2 and pHyg), from bovine papillomavirus (BPV, i.e. pdBPV and pBV-1MTHA), from Epstein-Barr Virus (EBV, i.e. p205 and pHEBo) or any other eukaryotic expression vector known in the art.

Other methods for providing growth factors to the area of transplantation include the implantation into the brain in proximity to the graft of any device which can provide an infusion of the factor to the surrounding cells.

In addition to the methods described above, numerous other methods are available for culturing and manipulation of CNS stem cells, see, for example, U.S. Pat. Nos. 6,777,233; 5,753,506 & 6,040,180 (describing propagation and long term in vitro culture of CNS stem cells —with retention of differentiation capacity, and selective differentiation into neurons, astrocytes and oligodendrocytes, for use in gene or cell therapy and screening for growth factors or drugs); U.S. Pat. No. 5,968,829 (describing isolation, characterization, proliferation, differentiation and transplantation of mammalian neural stem cells for treatment of conditions, such as, epilepsy, stroke, Huntington's disease, Alzheimer's disease, multiple sclerosis, or neuropathies). These methods can be readily adapted for use with the instant invention. All such descriptions are incorporated herein by reference.

3. Exemplary Uses

The instant invention provides the differentiated OLPs and oligodendrocytes differentiated therefrom, which may be use for a variety of medical and research purposes.

A. Therapeutic Uses for Treating Demyelination Diseases

Demyelination of central and peripheral neurons occurs in a number of pathologies and leads to improper signal conduction within the nervous systems. Myelin is a cellular sheath, formed by glial cells, that surrounds axons and axonal processes that enhances various electrochemical properties and provides trophic support to the neuron. Myelin is formed by Schwann cells in the PNS and by oligodendrocytes in the CNS. Among the various demyelinating diseases, MS is the most notable.

In both human demyelinating diseases and rodent models, there are substantial evidence that demyelinated neurons are capable of remyelination in vivo. In MS, for example, it appears that there are often cycles of de- and re-myelination. Similar observations in rodent demyelinating paradigms lead to the prediction that exogenously applied cells would be capable of remyelinating demyelinated axons. This approach has proven successful in a number of experimental conditions (see, for example, Freidman et al., Brain Research, 378: 142-146, 1986; Raine, et al., Laboratory Investigation 59: 467-476, 1988; Duncan et al., J. of Neurocytology, 17: 351-360, 1988). The sources of cells for some of these experiments included dissociated glial cell suspensions prepared from spinal cords (Duncan et al., supra), Schwann cell cultures prepared from sciatic nerve (Bunge et al., 1992, WO 92/03536; Blakemore and Crang, J. Neurol. Sci., 70: 207-223, 1985); cultures from dissociated brain tissue (Blakemore and Crang, Dev. Neurosci. 10: 1-11, 1988), oligodendrocyte precursor cells (Gumpel et al., Dev. Neurosci. 11: 132-139, 1989), O-2A cells (Wolswijk et al., Development 109: 691-608, 1990; Raff et al., Nature 3030: 390-396, 1983; Hardy et al., Development 111: 1061-1080, 1991), and immortalized O-2A cell lines (Almazan and McKay Brain Res. 579: 234-245, 1992).

Thus in one aspect, the present invention provides methods for treating mammalian diseases and conditions characterized by myelin destruction, such as in multiple sclerosis (MS), after viral infection, and other trauma or chemical insults-induced demyelination. The method comprising introducing OLPs and/or oligodendrocytes differentiated therefrom into a mammalian individual suffering from such diseases and conditions characterized by myelin destruction.

Another aspect of the invention provide a method for repairing damaged neural tissue in a relatively non-invasive fashion, that is, by inducing neural cells to proliferate and differentiate into oligodendrocytes in vivo, thereby averting the need for transplantation. The neural stem cells, OLP or ODC cells may be stimulated to proliferate/differentiate using the in vivo manipulation described above, such as co-expressing exogenous Olig genes and Nkx2.2 genes, optionally with other growth factors (supra).

Numerous neural stem cells (totipotent, pluripotent/multipotent) may be used for the subject invention. These neural stem cells possess the capability to further differentiate into OLPs or ODCs, and possible other cell types, such as neurons or astrocytes. Several such neural stem cells are described below for illustrative purpose only.

O-2A cells are glial progenitor cells which give rise in vitro only to oligodendrocytes and type II astrocytes. Cells which appear by immunostaining in vivo to have the O-2A phenotype have been shown to successfully remyelinate demyelinated neurons in vivo (Godfraind et al., J. Cell Biol. 109: 2405-2416, 1989). Injection of a large number of O-2A cells is required to adequately remyelinate all targeted neurons in vivo, since it appears that O-2A cells (like other glial cell preparations) do not continue to divide in vivo. O-2A progenitor cells can be grown in culture, but previous isolation technique employs optic nerve as starting material, thus limiting the amount of cells that can be obtained from adult tissues.

Although adult CNS neurons are not the best candidates for neurotransplantation, neurons from the adult PNS have been shown to survive transplantation, and to exert neurotrophic and gliotrophic effects on developing host neural tissue. One source of non-CNS neural tissue for transplantation is the adrenal medulla. In U.S. Pat. No. 4,980,174, transplantation of monoamine-containing cells isolated from adult rat pineal gland and adrenal medulla into rat frontal cortex led to the alleviation of learned helplessness, a form of depression in the host. In U.S. Pat. No. 4,753,635, chromaffin cells and adrenal medullary tissue derived from steers were implanted into the brain stem or spinal cord of rats and produced analgesia when the implanted tissue or cell was induced to release nociceptor interacting substances (i.e. catecholamines such as dopamine). Adrenal medullary cells have been autologously grafted into humans, and have survived, leading to mild to moderate improvement in symptoms (Watts, et al., "Adrenal-caudate transplantation in patients with Parkinson's Disease (PD):1-year follow-up," Neurology 39 Suppl 1: 127 [1989], Hurtig, et al., "Postmortem analysis of adrenal-medulla-to-caudate autograft in a patient with Parkinson's Disease," Annals of Neurology 25: 607-614 [1989]).

Another source of tissue for neurotransplantation is from cell lines. Cell lines are immortalized cells which are derived either by transformation of normal cells with an oncogene (Cepko, "Immortalization of neural cells via retrovirus-mediated oncogene transduction," Ann. Rev. Neurosci. 12:47-65 [1989]) or by the culturing of cells with altered growth characteristics in vitro (Ronnett, et al., "Human cortical neuronal cell line: Establishment from a patient with unilateral megalencephaly," Science 248:603-605 [1990]). Such cells can be grown in culture in large quantities to be used for multiple transplantations. Some cell lines have been shown to differentiate upon chemical treatment to express a variety of neuronal properties such as neurite formation, excitable membranes and synthesis of neurotransmitters and their receptors. Furthermore, upon differentiation, these cells appear to be amitotic, and therefore noncancerous.

Another approach to neurotransplantation involves the use of genetically engineered cell types or gene therapy. Using this method, a foreign gene or transgene can be introduced into a cell which is deficient in a particular enzymatic activity, thereby allowing the cell to express the gene. Cells which now contain the transferred gene can be transplanted to the site of neurodegeneration, and provide products such as neurotransmitters and growth factors (Rosenberg, et al., "Grafting genetically modified cells to the damaged brain: Restorative effects of NGF Expression," Science 242:1575-1578, [1988]) which may function to alleviate some of the symptoms of degeneration.

Thus the OLPs and oligodendrocytes may be obtained in large quantity by using the differentiation methods of the invention, for treating demyelination diseases in mammals.

B. Combination Therapy

The subject treatment methods may be used with one or more other treatment methods effective for the same disease conditions. This section describes several such treatments that can be used in a combination therapy with the subject treatment methods.

For example, U.S. Pat. No. 6,613,756 describes a method of treating multiple sclerosis, the method comprising treating a multiple sclerosis patient with a tetracycline derivative. For example, the tetracycline derivative may be selected from the group consisting of minocycline and doxycycline. The dose of tetracycline derivative is about 200 mg/day (±50 mg), for about 2-3 weeks. The method may be used prior to or at the same time as the patient receives a transplant of oligodendrocyte progenitor cells to repair chronic areas of demyelination.

U.S. Pat. No. 6,569,431 provides methods and compositions for inhibiting autoantibody binding in demyelinating disease such as multiple sclerosis. The compositions comprise immunoglobulin CDR3 sequences derived from combinatorial phage display libraries selected for high-affinity binding to myelin oligodendrocyte glycoprotein.

U.S. Pat. No. 6,548,061 describes novel compositions comprising the combined administration of serum complement proteins with complement-fixing antibodies. The antibodies specifically bind to one or more epitopes of myelin, and complement proteins. These compositions are useful for promoting regrowth, repair, and regeneration of neurons in the CNS of a mammalian subject. The compositions and method can be used following immediate or chronic injury.

U.S. Pat. No. 6,492,427 describes a method for increasing survival of ODCs, comprising administering an effective amount of a deprenyl compound to a patient in need thereof.

U.S. Pat. No. 6,150,345 provides a method for promoting survival of myelin producing cells (such as oligodendrocytes) comprising treating myelin producing cells with an effective amount of lysophosphatidic acid (LPA) to promote cell survival.

U.S. Pat. No. 6,333,033 describes a method of inhibiting demyelination associated with the binding of an autoantibody to a myelin oligodendrocyte glycoprotein (MOG) polypeptide, comprising the step of administering to a marmoset or human host, subject to a pathogenic MOG polypeptide—polyclonal autoantibody binding, an effective amount of a composition comprising a MOG polypeptide-specific antibody fragment not having a functional Fc portion and sufficient to specifically bind the MOG polypeptide and competitively inhibit the binding of the autoantibody to the MOG polypeptide, whereby the demyelination is inhibited.

U.S. Pat. No. 6,274,136 describes a method of treatment for autoimmune disease, comprising introducing one or more recombinant genes encoding self antigens which are the target of an autoimmune response. In particular the invention provides a method of designing and constructing a gene encoding an encephalogenic epitope of proteolipid protein, and to the in vivo expression of the gene product by a recombinant retroviral vector. The expression and secretion of the encephalogenic epitope ameliorates the histopathological and clinical characteristics of experimental autoimmune encephalomyelitis (EAE) in the mouse model for multiple sclerosis (MS).

U.S. Pat. No. 6,268,340 describes a method for regenerating oligodendrocytes in diseases such as multiple sclerosis, by administering human beta nerve growth factor (NGF-beta) by bolus injection. Treatment comprises 1-10 bolus injections in a dose of 0.05 to 5.0 mug/kg body at an interval of 1 to 21 days.

U.S. Pat. No. 6,203,788 provides a method for treating a demyelinating neurological disease such as MS in a mammal, comprising implanting in a mammal: (a) a cell adhesion modulating agent that is 6-50 amino acid residues in length, wherein the modulating agent comprises the sequence His-Ala-Val and at least one flanking amino acid residue present within an endogenous N-cadherin sequence selected from the group consisting of SEQ ID NOs: 3-5 of U.S. Pat. No. 6,203,788, and wherein the modulating agent inhibits N-cadherin-mediated cell adhesion; and (b) one or more cells selected from the group consisting of Schwann cells and oligodendrocyte progenitor cells from individuals not affected with a demyelinating disease; wherein the modulating agent and the cell(s) are implanted into the mammal's central nervous system in an amount sufficient to inhibit N-cadherin-mediated cell adhesion, thereby facilitating the cell(s) migration and treating a demyelinating neurological disease.

U.S. Pat. No. 5,885,584 provides a process to improve the growth and proliferation of oligodendrocytes or to improve and accelerate the remyelination of lesioned nerve fibers for diseases in which a demyelination of nerve fibers occurs, comprising administering a composition which contains an amount of NGF, NGF 2.5S or NGF 7S.

U.S. Pat. Nos. 5,219,837 & 5,574,009 provides methods for treating mammalian diseases and conditions characterized by myelin destruction. The invention provides methods for inducing myelin formation by myelin forming cells expressing retrovirus type 3 receptors comprising administering to such cells an effective amount of a compound bindable with the retrovirus type 3 receptor. The compounds preferably comprise antibodies and peptides, more preferably synthetic peptides.

C. Cancer Treatment

Oncogenic transformation and overproduction of cells in the oligodendrocyte lineage is known to leads to brain tumors such as oligodendrogliomas and glioblastoma multiforme, some of the most aggressive and intractable forms of cancer known. The prognosis for such brain tumors is usually very poor.

In addition, Olig gene overexpression may also be implicated in other forms of malignant tumors that do not originate in CNS. Although expression of Olig2 is normally restricted to neural tissues, overexpression of Olig2 has been shown in patients with precursor T-cell lymphoblastic lymphoma/leukemia (pre-T LBL). In the current study, Lin et al. (Cancer Res. 65(16): 7151-8, 2005) found that overexpression of Olig2 was not only found in oligodendroglioma samples and normal neural tissue, but also in a wide spectrum of malignant cell lines including leukemia, non-small cell lung carcinoma, melanoma, and breast cancer cell lines. Enforced overexpression of Olig2 in the thymus is only weakly (about 2%) oncogenic in transgenic mice, but oncogenesis is strongly enhanced when Lmo 1 is co-expressed, leading to 60% of the transgenic mice to develop pre-T LBL with large thymic tumor masses.

Thus the invention provides a method to treat cancer in an individual, comprising identifying an antagonists of OLP or ODC differentiation/proliferation, and administering an effective amount of the antagonists thus identified to the individual. While not wishing to be bound by any particular theory, the OLP or ODC differentiation/proliferation antagonists inhibit the function of Olig genes and/or Nkx2.2 genes, and may thus be useful for the treatment of diseases characterized by overexpression or excessive activity of the Olig genes.

The antagonists may be identified by assessing the ability and/or extent of a plurality of candidate compounds on differentiation of the neural stem cells to the OLP or ODC cells according to the methods of the invention, or on proliferation of the OLP or ODC cells thus obtained. The following section, inter alia, describes details of such screening assays.

Another aspect of the cancer treatment is differentiation therapy by inducing co-expressing of Nkx2.2 or Nkx2.5 (or their functional substitutes) in cancers characterized by overexpression of an Olig protein.

Degree of tumor differentiation has an important impact on the natural history of this disease and on treatment selection. The pattern of cancer spread is partially dependent on the degree of cellular differentiation. Well-differentiated tumors tend to limit their spread to the surface of the endometrium. In contrast, in patients with poorly differentiated tumors, invasion into surrounding tissues occurs much more frequently. Thus differentiation therapy may be effective in treating a large number of cancers.

For example, phenylacetate has recently been shown to suppress tumor growth and promote differentiation in experimental models. Thibault et al. (*A phase I and pharmacokinetic study of intravenous phenylacetate in patients with cancer. Cancer Res.* 54(7): 1690-4, 1994) reported that, in a phase I trial, phenylacetate was conducted in 17 patients with advanced solid tumors. Each patient received a single i.v. bolus dose followed by a 14-day continuous i.v. infusion of the drug. Twenty-one cycles of therapy were administered at four dose levels, achieved by increasing the rate of the continuous i.v. infusion. Three of nine patients with metastatic, hormone-refractory prostate cancer maintained stable prostatic specific antigen (PSA) levels for more than 2 months; another had less bone pain. One of six patients with glioblastoma multiforme, whose steroid dosage has remained unchanged for the duration of therapy, has sustained functional improvement for more than 9 months. These differentiation therapy has resulted in clinical improvement in some patients with advanced diseases.

The differentiation therapy of the instant invention is beneficial to treat (including lessening the symptoms, prolonging patient life-expectancy, and/or improving life quality) cancers characterized by Olig overexpression.

D. Drug Screening

Another aspect of the invention provides large quantities of OLPs and oligodendrocytes differentiated therefrom for research, such as for drug screening purposes and for the study of CNS function, dysfunction, and development.

The mature human nervous system is composed of billions of cells that are generated during development from a small number of precursors located in the neural tube. Due to the complexity of the mammalian CNS, the study of CNS developmental pathways, as well as alterations that occur in adult mammalian CNS due to dysfunction, has been difficult. Such areas would be better studied using relatively simple models of the CNS under defined conditions.

Generally, two approaches have been taken for studying cultured CNS cells: the use of primary neural cultures; and the use of neural cell lines. Primary mammalian neural cultures can be generated from nearly all brain regions providing that the starting material is obtained from fetal or early post-natal animals. In general, three types of cultures can be produced, enriched either in neurons, astrocytes, or oligodendrocytes. Primary CNS cultures have proven valuable for discovering many mechanisms of neural function and are used for studying the effects of exogenous agents on developing and mature cells.

While primary CNS cultures have many advantages, they suffer from two primary drawbacks. First, due to the limited proliferative ability of primary neural cells, new cultures must be generated from several different animals. While great care is usually taken to obtain tissue at identical states of development and from identical brain regions, it is virtually impossible to generate primary cultures that are identical. Hence, there exists a significant degree of variability from culture to culture.

A second disadvantage of primary cultures is that the tissue must be obtained from fetuses or early post-natal animals. If primary cultures are to be performed on a regular basis, this requires the availability of a large source of starting material. While this is generally not a problem for generating primary cultures from some species (e.g. rodents), it is for others (e.g. primates). Due to the limited supply and ethical concerns, the culturing of primary cells from primates (both human and non-human) is not practical.

Due to the limited proliferative ability of primary neural cells, the generation of a large number of homogenous cells for studies of neural function, dysfunction, and drug design/screening has previously not been achieved. Therefore, homogenous populations of cells that can generate a large number of progeny for the in vitro investigation of CNS function has been studied by the use of cell lines.

The generation of neural cell lines can be divided into two categories: 1) spontaneously occurring tumors, and 2) custom-designed cell lines. However, in view of the various deficiencies attendant with prior art methods of neural cell culturing, transplantation, and CNS models, a need exists in the art for a reliable source of unlimited numbers of undifferentiated neural cells for neurotransplantation and drug screening which are capable of differentiating into neurons, astrocytes, and oligodendrocytes.

The instant invention provides virtually unlimited supply of OLPs and ODCs, both for direct medical uses (e.g., cell transplantation), and for research and development.

One particularly useful type of research and development concerns the screening, preferably in large scale and with automation, drug candidates. For example, antagonists of OLP/ODC proliferation may become pharmaceutical compositions useful for the treatment of diseases characterized by OLP/ODC overproliferation, including oligodendroglioma or glioblastoma multiforme.

Thus another aspect of the invention provides a simple in vitro system for the screening of antagonists or candidate drug compounds that inhibits the differentiation of mammalian neural stem cells to OLPs or ODCs, or the proliferation of such OLPs or ODCs. Such drugs compounds are useful for treating diseases characterized by overproliferation of ODCs or cells derived therefrom, such as various cancers originating from ODCs or OLPs. Such drugs are also useful for treating diseases characterized by excessive Olig and/or Nkx2.2 function, such as in certain malignancies, including leukemia, non-small cell lung carcinoma, melanoma, and breast cancer (see Lin et al., *Cancer Res.* 65-(16): 7151-8, 2005).

In certain embodiments, the antagonist is a selective antagonist of ODC or OLP, but has significantly lesser or no effect on other cell types, such as astrocytes, neurons, etc.

Specific inhibitors of OLPs or ODCs may target Olig and/or Nkx2.2 genes, since human Olig1/2 genes are expressed strongly in oligodendroglioma, but is largely absent or only having low expression level in astrocytoma (Lu et al., *Proc. Nat. Acad. Sci.* 98: 10851-10856, 2001). These data also provided evidence that neoplastic cells of oligodendroglioma resemble oligodendrocytes or their progenitor cells and may derive from cells of this lineage. The specific or selective antagonists thus identified have stronger therapeutic index, and can be used at relatively high dosages without causing intolerable side-effects.

The subject screening method for identifying antagonists for oligodendrocyte proliferation comprises contacting a candidate compound with a subject oligodendrocyte or OLP, and comparing the proliferation of the oligodendrocyte or OLP before vs. after contacting the candidate compound, wherein a reduced proliferation rate indicates that the candidate compound is a potential growth inhibitor of the subject oligodendrocyte or OLP.

In one embodiment, the method further comprising assessing the general toxicity of the antagonist thus identified on other cell types, such as neurons, astrocytes, epithelial cells, endothelial cells, and/or fibroblasts.

In one embodiment, the method further comprising assessing the in vitro and/or in vivo killing effect of the antagonist thus identified on established cancer or cancer cell lines, such as those from oligodendroglioma, or glioblastoma multiforme. The antagonist is a selective antagonist of OLP or ODC proliferation if the antagonist is substantially more effective in inhibiting the proliferation of OLP or ODC than the other cell types.

In one embodiment, the antagonist inhibits OLP or ODC proliferation (e.g., measured by % of cell number increase over a period of time) or differentiation (e.g., measured by % of cells expressing one or more selected OLP/ODC differentiation markers) by at least about 10%, at least about 20%, at least about 25%, at least about 30%, at least about 35%, at least about 40%, at least about 45%, at least about 50%, at least about 55%, at least about 60%, at least about 65%, at least about 70%, at least about 80%, at least about 90%, or more, when compared to a control in the absence of the test agent. The OLP/ODC differentiation markers may include one or more of O4, galactocerebroside (GalC), and/or myelin basic protein (MBP).

In one embodiment, the antagonist is at least 50%, 75%, 1-fold, 2-fold, 5-fold, 10-fold or more effective in inhibiting OLP or ODC proliferation than inhibiting the proliferation of one of said other cell types.

The effectiveness may be measured by $EC_{50}$, which represents the concentration of the candidate compound that gives rise to 50% of the maximum inhibition.

The terms "candidate agent," "test agent," "agent", "substance" and "compound" are used interchangeably herein and describe a variety of agents that may be screened using the above methods.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modeling. For example, numerous means are available for random and directed synthesis of a wide variety of organic compounds and biomolecules, including expression of randomized oligonucleotides and oligopeptides.

Screening may be directed to known pharmacologically active compounds and chemical analogs thereof, or to new agents with unknown properties such as those created through rational drug design.

A variety of other reagents may be included in screening assays. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, anti-microbial agents, etc. may be used. Incubations are performed at any suitable temperature, typically between 4 and 40° C. Incubation periods are selected for optimum activity, but may also be optimized to facilitate rapid high-throughput screening. Typically between 0.1 and 1 hour will be sufficient.

Candidate agents may also include biopolymers, including nucleic acids (e.g. DNA, RNA, cDNA, plasmids and this like), for example those encoding Olig genes or Nkx2.2 genes, or antisense nucleic acids and the like, carbohydrates, lipids (e.g. lipids that inhibit the activity thereof) and proteins and polypeptides, (such as Olig proteins or Nkx2.2 proteins or an antibody specific therefor).

Agents that have an effect in an assay method of the invention may be further tested for cytotoxicity, bioavailability, and the like, using well known assays. Agents that have an effect in an assay method of the invention may be subjected to directed or random and/or directed chemical modifications, such as acylation, alkylation, esterification, amidification, etc. to produce structural analogs. Such structural analogs include those that increase bioavailability, and/or reduced cytotoxicity. Those skilled in the art can readily envision and generate a wide variety of structural analogs, and test them for desired properties such as increased bioavailability and/or reduced cytotoxicity and/or ability to cross the blood-brain barrier.

The compounds identified in the screen will demonstrate the ability to selectively modulate the expression of Olig and/or Nkx2.2. These compounds include but are not limited to nucleic acid encoding Olig and/or Nkx2.2 genes and homologues, analogues, and deletions thereof, as well as antisense, ribozyme, triple helix, antibody, and polypeptide molecules and small inorganic molecules.

Any of the identified compounds can be administered to an animal host, including a human patient, by itself, or in pharmaceutical compositions where it is mixed with suitable carriers or excipient(s) at doses therapeutically effective to treat or ameliorate a variety of disorders (such as those described herein), including those characterized by insufficient, aberrant, or excessive Olig and/or Nkx2.2 activity. A therapeutically effective dose further refers to that amount of the compound sufficient to result in amelioration of symptoms associated with such disorders. Techniques for formulation and administration of the compounds of the instant application may be found in "Remington's Pharmaceutical Sciences," Mack Publishing Co., Easton, Pa., latest edition.

The compounds of the invention may be designed or administered for tissue specificity. If the compound comprises a nucleic acid molecule, including those comprising an expression vector, it may be linked to a regulatory sequence which is specific for the target tissue, such as the brain, skin, joints, bladder, kidney, liver, ovary, etc. by methods which are known in the art including those set forth in Hart, 1994, Ann. Oncol., 5 Suppl 4: 59-65; Dahler et al., 1994, Gene, 145: 305-310; DiMaio et al., 1994, Surgery, 116:205-213; Weichselbaum et al., Cancer Res., 54:4266-4269; Harris et al., 1994, Cancer, 74 (Suppl. 3):1021-1025; Rettinger et al., Proc. Nat'l. Acad. Sci. USA, 91:1460-1464; and Xu et al, Exp. Hematol., 22:223-230; Brigham et al., 1994, Prog. Clin. Biol. Res., 388:361-365. The compounds of the invention may be targeted to specific sites of lesion by direct injection to those sites. Compounds designed for use in the central nervous system should be able to cross the blood brain barrier or be suitable for administration by localized injection. Such compounds which remain within the bloodstream may be prepared by methods well known in the art including those described more fully in McIntire, 1994, Annals Biomed. Engineering, 22:2-13.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the $IC_{50}$ (the dose where 50% of the cells show the desired effects) as determined in cell culture. Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p 1). Dosage amount and interval may be adjusted individually to provide plasma levels of the active moiety which are sufficient to maintain the desired effects.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars; including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection (e.g., bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. Naturally, the proportions of a co-solvent system may be varied considerably without destroying its solubility and toxicity characteristics. Furthermore, the identity of the co-solvent components may be varied.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

Suitable routes of administration may, for example, include oral, rectal, transmucosal, transdermal, or intestinal administration; parenteral delivery, including intramuscular, subcutaneous, intramedullary injections, as well as intrathecal, direct intraventricular, intravenous, intraperitoneal, intranasal, or intraocular injections.

Alternately, one may administer the compound in a local rather than systemic manner, for example, via injection of the compound directly into an affected area, often in a depot or sustained release formulation.

Furthermore, one may administer the drug in a targeted drug delivery system, for example, in a liposome coated with an antibody specific for affected cells. The liposomes will be targeted to and taken up selectively by the cells.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition. Suitable conditions indicated on the label may include treatment of a disease such as one characterized by insufficient, aberrant, or excessive Olig and/or Nkx2.2 activity.

4. Grafting Cells/Tissues

The subject OLP cells can be used in a variety of applications (see above). For example, the methods of the invention described herein can be used to differentiate specific populations of stem cells useful for transplantation, and to expand the number of available oligodendritic precursor cells derived from a variety of culture systems.

Preferably cellular division in such cells from such a source would be epigenetically regulated and a suitable number of cells could be efficiently prepared in sufficient numbers for transplantation. The cells should be suitable in autografts, xenografts, and allografts without a concern for tumor formation. There exists a need for the isolation, perpetuation and transplantation of autologous neural cells from the juvenile or adult brain that are capable of differentiating into neurons and glia.

Methods of grafting cells are now well known to those of skill in art (see, for example, U.S. Pat. No. 5,762,926; U.S. Pat. No. 5,650,148; U.S. Pat. No. 5,082,670, all incorporated herein by reference). Neural transplantation or grafting involves transplantation of cells into the central nervous system or into the ventricular cavities or subdurally onto the surface of a host brain. Conditions for successful transplantation include: 1) viability of the implant; 2) retention of the graft at the site of transplantation; and 3) minimum amount of pathological reaction at the site of transplantation. The cells can be from the patient (autologous) or from a foreign individual (same or different species, preferably from the same species).

Methods for transplanting various nerve tissues, for example embryonic brain tissue, into host brains have been described in *Neural Grafting in the Mammalian CNS*, Bjorklund and Stenevi, eds., (1985) Das, Ch. 3 pp. 23-30; Freed, Ch. 4, pp. 31-40; Stenevi et al., Ch. 5, pp. 41-50; Brundin et al., Ch. 6, pp. 51-60; David et al., Ch. 7, pp. 61-70; Seiger, Ch. 8, pp. 71-77 (1985), incorporated by reference herein. These procedures include intraparenchymal transplantation, i.e., within the host brain (as compared to outside the brain or extraparenchymal transplantation) achieved by injection or deposition of tissue/cells within the host brain so as to be opposed to the brain parenchyma at the time of transplantation (Das, supra).

The two main procedures for intraparenchymal transplantation are: 1) injecting the donor cells within the host brain parenchyma, or 2) preparing a cavity by surgical means to expose the host brain parenchyma and then depositing the graft into the cavity (Das, supra). Both methods provide parenchymal apposition between the graft and host brain tissue at the time of grafting, and both facilitate anatomical integration between the graft and host brain tissue. This is of importance if it is required that the graft become an integral part of the host brain and to survive for the life of the host.

Alternatively, the graft may be placed in a ventricle, e.g., a cerebral ventricle or subdurally, i.e., on the surface of the host brain where it is separated from the host brain parenchyma by the intervening pia mater or arachnoid and pia mater. Grafting to the ventricle may be accomplished by injection of the donor cells, or by growing the cells in a substrate such as 3% collagen to form a plug of solid tissue which may then be implanted into the ventricle to prevent dislocation of the graft. For subdural grafting, the cells may be injected around the surface of the brain after making a slit in the dura. Injections into selected regions of the host brain may be made by drilling a hole and piercing the dura to permit the needle of a microsyringe to be inserted. The microsyringe is preferably mounted in a stereotaxic frame and three dimensional stereotaxic coordinates are selected for placing the needle into the desired location of the brain or spinal cord.

The subject donor cells may also be introduced into the putamen, nucleus basalis, hippocampus cortex, striatum or caudate regions of the brain, as well as the spinal cord.

For grafting, the cell suspension is drawn up into the syringe and administered to anesthetized graft recipients. Multiple injections may be made using this procedure. The age of the donor tissue, i.e., the developmental stage, may affect the success of cell survival after grafting.

The cellular suspension procedure thus permits grafting of donor cells to any predetermined site in the brain or spinal cord, is relatively non-traumatic, allows multiple grafting simultaneously in several different sites or the same site using the same cell suspension, and permits mixtures of cells from different anatomical regions. Multiple grafts may consist of a mixture of cell types, and/or a mixture of transgenes inserted into the cells. Preferably from approximately $10^4$ to approximately $10^8$ cells are introduced per graft.

For transplantation into cavities, which may be preferred for spinal cord grafting, tissue is removed from regions close to the external surface of the CNS to form a transplantation cavity, for example by removing bone overlying the brain and stopping bleeding with a material such a gelfoam (Stenevi et al., *Brain Res.* 114: 1-20, 1976). Suction may be used to create the cavity. The graft is then placed in the cavity. More than one transplant may be placed in the same cavity using injection of cells or solid tissue implants.

Grafting of donor cells into a traumatized brain will require different procedures, e.g., the site of injury must be cleaned and bleeding stopped before attempting to graft. In addition, the donor cells should possess sufficient growth potential to fill any lesion or cavity in the host brain to prevent isolation of the graft in the pathological environment of the traumatized brain.

In one embodiment, the cells generated by the methods herein are used on an animal model of a disease, for example, in pre-clinical trials.

A rodent model of Multiple Sclerosis, EAE, may be generated. Experimental Autoimmune Encephalomyelitis (EAE), also called Experimental Allergic Encephalomyelitis, is an animal model of Multiple Sclerosis. Animal models of human diseases are diseases of non-human species (often rodents) which closely resemble their human counterparts and are be studied with a view to better understanding and treating the human form. EAE is not multiple sclerosis, nor is it a single disease in a single species, but its different forms resemble the various forms and stages of MS very closely in a large number of ways.

EAE is an acute or chronic-relapsing, acquired, inflammatory and demyelinating autoimmune disease. The animals are injected with the whole or parts of various proteins that make up myelin, the insulating sheath that surrounds nerve cells (neurons). These proteins induce an autoimmune response in the animals—that is the animal's immune system mounts an attack on its own myelin as a result of exposure to the injection. The animals develop a disease process that closely resembles MS in humans. EAE has been induced in a number of different animal species including mice, rats, guinea pigs, rabbits, macaques, rhesus monkeys and marmosets. For various reasons including the number of immunological tools, the availability, lifespan and fecundity of the animals and the resemblance of the induced disease to MS, mice and rats are the most commonly used species.

The animals are in-bred to reliably produce susceptibility to EAE in the animals. As with humans and MS, not all mice or rats will have a natural propensity to acquire EAE. Moreover, different breeds will develop different forms of EAE, some of which act as good models for the different human forms of MS. Different EAE forms are also used as models for the different stages of MS.

Several proteins or parts of proteins (antigens) are used to induce EAE including: Myelin Basic Protein (MBP), Proteolipid Protein (PLP/DM20), and Myelin Oligodendrocyte Glycoprotein (MOG). These induced EAE in animals may be used to test the subject treatments for MS for efficacy and/or safety before clinical trial in human.

Because the generations times of most of the EAE species are short, and because they breed very fast, large populations of such animals can be turned over in short periods of time.

Another commonly utilized experimental model of multiple sclerosis is induced by Theiler's murine encephalomyelitis virus (TMEV). In the TMEV model, spinal cord demyelination is influenced by the immune response to virus infection and is therefore continuously sensitive to immunomodulation.

Using such animal models, a baseline behavior/symptom can be established. After that, the cells grown in the present invention can then be transplanted into the animal model as described herein above. Any decrease in severity, duration, and/or progression of the symptoms would be indicative of the cellular transplant having an appropriate therapeutic value. Other animal models are known in the art and can be used in conjunction with the methods herein.

EXAMPLES

The following example is included to demonstrate preferred embodiments of the invention. It should be appreciated by those of skill in the art that the techniques disclosed in the example which follows represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

We performed experiments to show that in mammals, co-expression of the Olig genes and Nkx2.2 genes enhanced oligodendrocyte precursor formation. Specifically, cultured E13.5 rat spinal cord neural stem cells were transfected by either Olig2 or Nkx2.2 alone, or by both genes, or mock-transfected. The expression of the oligodendrocyte (ODC) marker O4 was then assessed in the transfected cells. The results indicated that the combination of Olig2+Nkx2.2, when co-transfected into E13.5 rat spinal cord neural stem cells, indeed enhanced oligodendrocyte formation. The percentage of O4-expressing cells was 2-3 times higher (15%, as compared to 5-8% in control cells) in cells co-transfected by both genes. This result was statistically significant ($p<0.05$). See FIG. 1. Thus in the mammalian system, the Olig genes in combination with Nkx2.2 promotes oligodendrocyte differentiation in stem cells.

Equivalents

Those skilled in the art will recognize, or be able to ascertain using no more than routine experimentation, numerous equivalents to the specific method and reagents described herein, including alternatives, variants, additions, deletions, modifications and substitutions. Such equivalents are considered to be within the scope of this invention and are covered by the following claims.

All publications mentioned herein are incorporated herein by reference, for the purpose of describing and disclosing the subject components of the invention that are described in the publications, which components might be used in connection with the presently described invention.

The invention claimed is:

1. A method to promote in vitro differentiation of a neural stem cell, a neural progenitor cell, or an embryonic stem cell from a mammal to an oligodendrocyte precursor (OLP) or an oligodendrocyte (ODC), comprising co-expressing in said neural stem cell, neural progenitor cell, or embryonic stem cell an exogenous Olig gene and an exogenous Nkx2.2 gene.

2. The method of claim 1, wherein the neural stem cell grows in a monolayer culture, or as a proliferating cell in a neurosphere.

3. The method of claim 1, wherein said neural stem cell, neural progenitor cell, or embryonic stem cell differentiates into an OLP or ODC.

4. The method of claim 1, wherein the OLP or ODC expresses O4, galactocerebroside (GalC), PLP/DM20, PDGFRα, Sox10, GST-π, CNP (2'3'-cyclic nucleotide-3'-phospho-hydrolase), RIP (oligodendrocyte specific molecule), and/or myelin basic protein (MBP).

5. The method of claim 1, wherein the Olig gene is a polynucleotide encoding an Olig polypeptide at least about 90% identical to the Olig1, Olig2, and/or Olig3 protein(s) of the mammal, said Olig polypeptide promotes differentiation to OLP or ODC when co-expressed with the Nkx2.2 gene.

6. The method of claim 1, wherein the Olig gene encodes the Olig1, Olig2, or Olig3 protein of the mammal.

7. The method of claim 1, wherein the Nkx2.2 gene is a polynucleotide encoding a polypeptide at least about 90% identical to the Nkx2.2 or Nkx2.5 protein of the mammal, said polypeptide promotes differentiation to OLP or ODC when co-expressed with the Olig gene.

8. The method of claim 1, wherein the exogenous Olig gene and/or the exogenous Nkx2.2 gene are under the control of a constitutive promoter or an inducible promoter.

9. The method of claim 1, wherein the Olig gene and/or the Nkx2.2 gene are transgenes.

* * * * *

SEQUENCE LISTING

<160> NUMBER OF SEQ ID NOS: 14

<210> SEQ ID NO 1
<211> LENGTH: 12
<212> TYPE: PRT
<213> ORGANISM: Artificial Sequence
<220> FEATURE:
<223> OTHER INFORMATION: EGF (epidermal growth factor)-derived
      internalization peptides

<400> SEQUENCE: 1

Cys Met His Ile Glu Ser Leu Asp Ser Tyr Thr Cys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: EGF (epidermal growth factor)-derived
      internalization peptides

<400> SEQUENCE: 2

Cys Met Tyr Ile Glu Ala Leu Asp Lys Tyr Ala Cys
1               5                   10

<210> SEQ ID NO 3
<211> LENGTH: 32
<212> TYPE: PRT
<213> ORGANISM: Artificial Sequence
<220> FEATURE:
<223> OTHER INFORMATION: pH-dependent membrane-binding internalizing
      peptide
<220> FEATURE:
<221> NAME/KEY: VARIANT
<222> LOCATION: 1, 2, 3
<223> OTHER INFORMATION: Xaa = Any Amino Acid

<400> SEQUENCE: 3

Xaa Xaa Xaa Glu Ala Ala Leu Ala Glu Ala Leu Ala Glu Ala Leu Ala
1               5                   10                  15

Glu Ala Leu Ala Glu Ala Leu Ala Glu Ala Leu Glu Ala Leu Ala Ala
            20                  25                  30

<210> SEQ ID NO 4
<211> LENGTH: 8
<212> TYPE: PRT
<213> ORGANISM: Artificial Sequence
<220> FEATURE:
<223> OTHER INFORMATION: a peptide substrate for N-myristoyl
      transferase

<400> SEQUENCE: 4

Gly Asn Ala Ala Ala Ala Arg Arg
1               5

<210> SEQ ID NO 5
<211> LENGTH: 10
<212> TYPE: PRT
<213> ORGANISM: Artificial Sequence
<220> FEATURE:
<223> OTHER INFORMATION: laminin-derived peptide

<400> SEQUENCE: 5

Cys Asp Pro Gly Tyr Ile Gly Ser Arg Cys
1               5                   10

<210> SEQ ID NO 6
<211> LENGTH: 75
<212> TYPE: DNA
<213> ORGANISM: Artificial Sequence
<220> FEATURE:
<223> OTHER INFORMATION: Nucleic acid encoding integrin-binding RGD
      peptide / SV40 nuclear localization signal

<400> SEQUENCE: 6
catatggutg actgccgtgg cgatatgttc ggttgcggtg ctcctccaaa aagaagaga    60 aaggtagctg gattc                                                   75

<210> SEQ ID NO 7
<211> LENGTH: 24
<212> TYPE: PRT
<213> ORGANISM: Artificial Sequence
<220> FEATURE:
<223> OTHER INFORMATION: RGD peptide / SV40 nuclear localization signal

<400> SEQUENCE: 7

Met Gly Gly Cys Arg Gly Asp Met Phe Gly Cys Gly Ala Pro Pro Lys
1               5                   10                  15

Lys Lys Arg Lys Val Ala Gly Phe
            20

<210> SEQ ID NO 8
<211> LENGTH: 222
<212> TYPE: DNA
<213> ORGANISM: Artificial Sequence
<220> FEATURE:
<223> OTHER INFORMATION: Nucleic acid encoding HIV-1 tat(1-72)
      polypeptide

<400> SEQUENCE: 8
catatggagc cagtagatcc tagactagag ccctggaagc atccaggaag tcagcctaaa    60
actgcttgta ccaattgcta ttgtaaaaag tgttgctttc attgccaagt gtttcataac   120
aaaagccctt ggcatctcct atggcaggaa gaagcgagac agcgacgaag acctcctcaa   180
ggcagtcaga ctcatcaagt ttctctaagt aagcaaggat tc                      222

<210> SEQ ID NO 9
<211> LENGTH: 72
<212> TYPE: PRT
<213> ORGANISM: Artificial Sequence
<220> FEATURE:
<223> OTHER INFORMATION: HIV-1 tat(1-72) polypeptide

<400> SEQUENCE: 9

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln
65                  70

<210> SEQ ID NO 10
<211> LENGTH: 912

<212> TYPE: DNA
<213> ORGANISM: Artificial Sequence
<220> FEATURE:
<223> OTHER INFORMATION: Nucleic acid encoding HSV-1 VP22 polypeptide

<400> SEQUENCE: 10

```
catatgacct ctcgccgctc cgtgaagtcg ggtccgcggg aggttccgcg cgatgagtac      60
gaggatctgt actacacccc gtcttcaggt atggcgagtc ccgatagtcc gcctgacacc     120
tcccgccgtg gcgccctaca gacacgctcg cgccagaggg gcgaggtccg tttcgtccag     180
tacgacgagt cggattatgc cctctacggg ggctcgtcat ccgaagacga cgaacacccg     240
gaggtccccc ggacgcggcg tcccgtttcc ggggcggttt tgtccggccc ggggcctgcg     300
cgggcgcctc cgccaccgc tgggtccgga ggggccggac gcacacccac caccgccccc      360
cgggcccccc gaacccagcg ggtggcgact aaggcccccg cggccccggc ggcggagacc     420
acccgcggca ggaaatcggc ccagccagaa tccgccgcac tcccagacgc ccccgcgtcg     480
acggcgccaa cccgatccaa gacacccgcg caggggctgg ccagaaagct gcactttagc     540
accgccccc caaaccccga cgcgccatgg accccccggg tggccggctt taacaagcgc      600
gtcttctgcg ccgcggtcgg gcgcctggcg gccatgcatg cccggatggc ggcggtccag     660
ctctgggaca tgtcgcgtcc gcgcacagac gaagacctca cgaactcct tggcatcacc      720
accatccgcg tgacggtctg cgagggcaaa aacctgcttc agcgcgccaa cgagttggtg     780
aatccagacg tggtgcagga cgtcgacgcg ccacggcga ctcgagggcg ttctgcggcg      840
tcgcgccca ccgagcgacc tcgagcccca gcccgctccg cttctcgccc agacggccc      900
gtcgaggaat tc                                                         912
```

<210> SEQ ID NO 11
<211> LENGTH: 301
<212> TYPE: PRT
<213> ORGANISM: Artificial Sequence
<220> FEATURE:
<223> OTHER INFORMATION: HSV-1 VP22 polypeptide

<400> SEQUENCE: 11

```
Met Thr Ser Arg Arg Ser Val Lys Ser Gly Pro Arg Glu Val Pro Arg
 1               5                  10                  15

Asp Glu Tyr Glu Asp Leu Tyr Tyr Thr Pro Ser Ser Gly Met Ala Ser
            20                  25                  30

Pro Asp Ser Pro Pro Asp Thr Ser Arg Arg Gly Ala Leu Gln Thr Arg
        35                  40                  45

Ser Arg Gln Arg Gly Glu Val Arg Phe Val Gln Tyr Asp Glu Ser Asp
    50                  55                  60

Tyr Ala Leu Tyr Gly Gly Ser Ser Ser Glu Asp Asp Glu His Pro Glu
65                  70                  75                  80

Val Pro Arg Thr Arg Arg Pro Val Ser Gly Ala Val Leu Ser Gly Pro
                85                  90                  95

Gly Pro Ala Arg Ala Pro Pro Pro Ala Gly Ser Gly Gly Ala Gly
            100                 105                 110

Arg Thr Pro Thr Thr Ala Pro Arg Ala Pro Arg Thr Gly Arg Val Ala
        115                 120                 125

Thr Lys Ala Pro Ala Ala Pro Ala Ala Glu Thr Thr Arg Gly Arg Lys
    130                 135                 140

Ser Ala Gln Pro Glu Ser Ala Ala Leu Pro Asp Ala Pro Ala Ser Thr
145                 150                 155                 160
```

-continued

```
Ala Pro Thr Arg Ser Lys Thr Pro Ala Gln Gly Leu Ala Arg Lys Leu
            165                 170                 175

His Phe Ser Thr Ala Pro Pro Asn Pro Asp Ala Pro Trp Thr Pro Arg
        180                 185                 190

Val Ala Gly Phe Asn Lys Arg Val Phe Cys Ala Ala Val Gly Arg Leu
            195                 200                 205

Ala Ala Met His Ala Arg Met Ala Ala Val Gln Leu Trp Asp Met Ser
    210                 215                 220

Arg Pro Arg Thr Asp Glu Asp Leu Asn Glu Leu Leu Gly Ile Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Val Val Gln Asp Val Asp Ala Ala Thr Ala
                260                 265                 270

Thr Arg Gly Arg Ser Ala Ala Ser Arg Pro Thr Glu Arg Pro Arg Ala
            275                 280                 285

Pro Ala Arg Ser Ala Ser Arg Pro Arg Arg Pro Val Glu
        290                 295                 300
```

<210> SEQ ID NO 12
<211> LENGTH: 120
<212> TYPE: DNA
<213> ORGANISM: Artificial Sequence
<220> FEATURE:
<223> OTHER INFORMATION: Nucleic acid encoding the C-terminal domain of
      the VP22 protein

<400> SEQUENCE: 12

```
catatggacg tcgacgcggc cacggcgact cgagggcgtt ctgcggcgtc gcgccccacc    60
gagcgacctc gagccccagc ccgctccgct tctcgcccca gacggcccgt cgaggaattc   120
```

<210> SEQ ID NO 13
<211> LENGTH: 37
<212> TYPE: PRT
<213> ORGANISM: Artificial Sequence
<220> FEATURE:
<223> OTHER INFORMATION: the C-terminal domain of the VP22 protein

<400> SEQUENCE: 13

```
Met Asp Val Asp Ala Ala Thr Ala Thr Arg Gly Arg Ser Ala Ala Ser
1               5                   10                  15

Arg Pro Thr Glu Arg Pro Arg Ala Pro Ala Arg Ser Ala Ser Arg Pro
            20                  25                  30

Arg Arg Pro Val Glu
        35
```

<210> SEQ ID NO 14
<211> LENGTH: 16
<212> TYPE: PRT
<213> ORGANISM: Artificial Sequence
<220> FEATURE:
<223> OTHER INFORMATION: Linker peptide

<400> SEQUENCE: 14

```
Gly Gly Gly Ser Gly Gly Gly Ser Gly Gly Gly Ser Gly Gly Gly Ser
1               5                   10                  15
```